United States Patent
James, Jr.

(10) Patent No.: US 10,973,412 B1
(45) Date of Patent: Apr. 13, 2021

(54) SYSTEM FOR PRODUCING CONSISTENT MEDICAL IMAGE DATA THAT IS VERIFIABLY CORRECT

(71) Applicant: TRUE-SEE SYSTEMS, LLC, New Orleans, LA (US)

(72) Inventor: Francis Godwin James, Jr., New Orleans, LA (US)

(73) Assignee: TRUE-SEE SYSTEMS, LLC, New Orleans, LA (US)

( * ) Notice: Subject to any disclaimer, the term of this patent is extended or adjusted under 35 U.S.C. 154(b) by 0 days.

(21) Appl. No.: 14/209,557

(22) Filed: Mar. 13, 2014

Related U.S. Application Data

(60) Provisional application No. 61/799,843, filed on Mar. 15, 2013.

(51) Int. Cl.
*A61B 5/00* (2006.01)
*A61B 90/96* (2016.01)

(52) U.S. Cl.
CPC .......... *A61B 5/0077* (2013.01); *A61B 5/0071* (2013.01); *A61B 5/445* (2013.01); *A61B 90/96* (2016.02); *A61B 2576/00* (2013.01)

(58) Field of Classification Search
CPC ... A61B 5/0077; A61B 5/445; A61B 2576/00; A61B 5/0059–0075; A61B 90/90–96
See application file for complete search history.

(56) References Cited

U.S. PATENT DOCUMENTS

| | | | | |
|---|---|---|---|---|
| 5,027,587 A * | 7/1991 | Ramsey | .................... | B07C 1/00 53/131.1 |
| 5,836,872 A * | 11/1998 | Kenet et al. | .................. | 600/306 |
| 6,993,167 B1 * | 1/2006 | Skladnev | ............. | A61B 5/0059 382/128 |
| 8,123,704 B2 * | 2/2012 | Richards | ...................... | 600/587 |
| 8,823,934 B2 * | 9/2014 | Chhibber et al. | ............. | 356/366 |
| 8,848,988 B2 * | 9/2014 | Plickert | ............. | G01N 21/8483 382/128 |
| 8,849,380 B2 * | 9/2014 | Patwardhan | .................. | 600/476 |
| 2002/0123671 A1 * | 9/2002 | Haaland | ............... | A61B 5/0002 600/300 |
| 2002/0140990 A1 * | 10/2002 | Liu | .......................... | G02B 7/28 358/406 |
| 2003/0004946 A1 * | 1/2003 | VanDenAvond | ....... | G06Q 10/10 |
| 2003/0055341 A1 * | 3/2003 | Banerjee | ............. | G01N 33/533 600/476 |
| 2003/0216836 A1 * | 11/2003 | Treat et al. | ................... | 700/245 |

(Continued)

OTHER PUBLICATIONS

Acha et al, Segmentation and Classification of burn images by color and texture information, Journal of Biomedical Optics, 10(3) May/Jun. 2005, pp. 034014-1-034014-11.*

*Primary Examiner* — Oommen Jacob

(74) *Attorney, Agent, or Firm* — AdamsIP, LLC

(57) ABSTRACT

The invention is a complete method for producing consistent medical image data that is verifiably correct, comprising taking a series of photos of the same wound, each photo being taken with a calibration slate which appears in the photo; and calibrating the photos for color using the calibration slate, the calibration slate including a means of quantifying focus by means of a focus chart with a grading system included on the slate, the slate having a front side and a back side, and an adhesive attached to the back side of the calibration slate, to facilitate attaching the calibration slate to a subject.

20 Claims, 23 Drawing Sheets

(56) References Cited

U.S. PATENT DOCUMENTS

| | | | | |
|---|---|---|---|---|
| 2003/0225324 A1* | 12/2003 | Anderson | ............... | A61B 5/01 600/364 |
| 2004/0000246 A1* | 1/2004 | Keane | .................. | G06Q 40/00 101/483 |
| 2005/0261551 A1* | 11/2005 | Couvillon, Jr. | .... | A61B 1/00059 600/118 |
| 2007/0242877 A1* | 10/2007 | Peters | ...................... | G01J 3/46 382/167 |
| 2007/0287191 A1* | 12/2007 | Stiene | ................... | C12Q 1/006 436/150 |
| 2008/0175430 A1* | 7/2008 | Fan | ...................... | G06T 1/0028 382/100 |
| 2009/0317002 A1* | 12/2009 | Dein | ........................ | 382/224 |
| 2010/0121201 A1* | 5/2010 | Papaioannou | ............... | 600/477 |
| 2010/0195902 A1* | 8/2010 | Horovitz | ............... | H04N 1/603 382/162 |
| 2011/0117025 A1* | 5/2011 | Dacosta | ............... | A61B 5/0059 424/9.6 |
| 2011/0293153 A1* | 12/2011 | Plickert | ............. | G01N 21/8483 382/128 |
| 2012/0253122 A1* | 10/2012 | Minetoma | ........... | A61B 1/0653 600/109 |

* cited by examiner

FIGURE: 1a – Sample Calibration Slate 1a
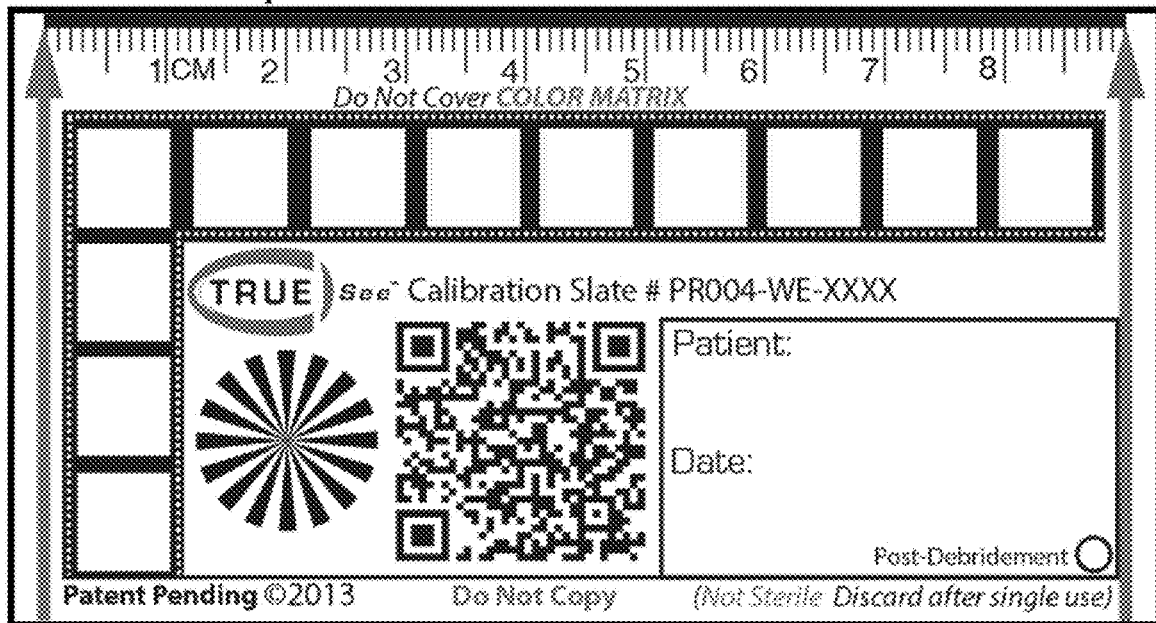
FIGURE: 1b – Sample Calibration Slate 1b
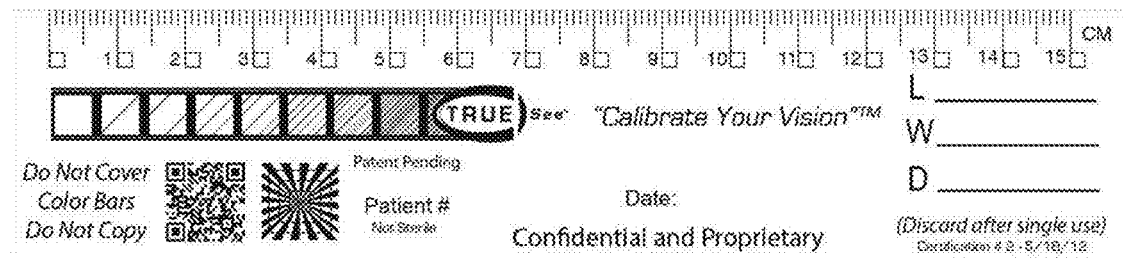
Figure 1c - Sample Calibration Slate 1c
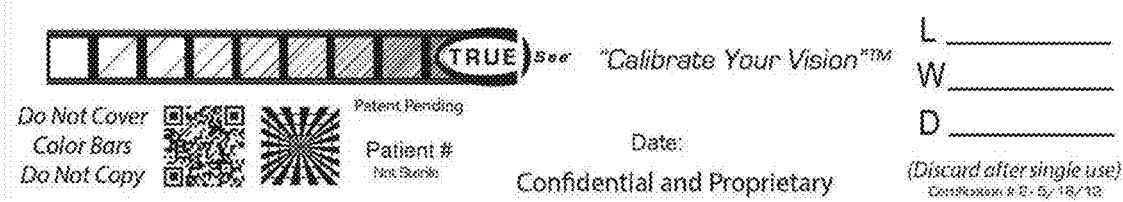
Figure 1d - Sample Calibration Slate 1d
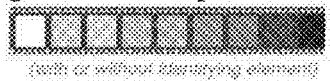

FIGURE: 2 -- Annotated Calibration Slate
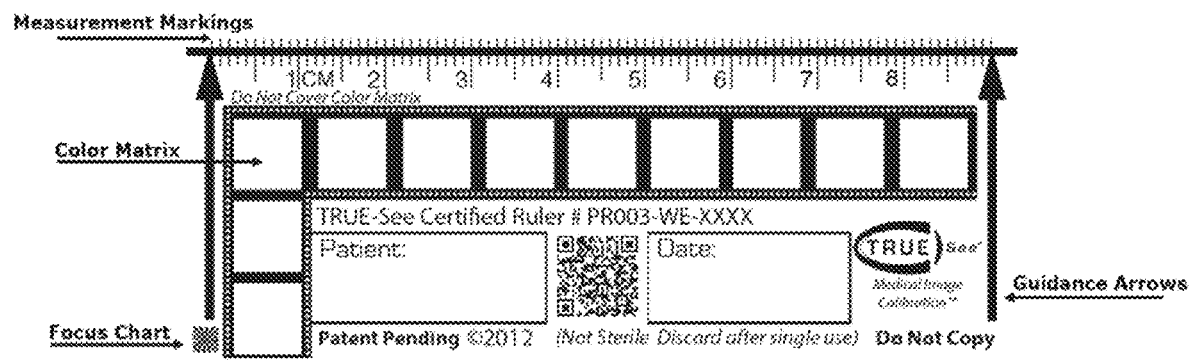
FIGURE: 3 -- Examples of Focus Charts
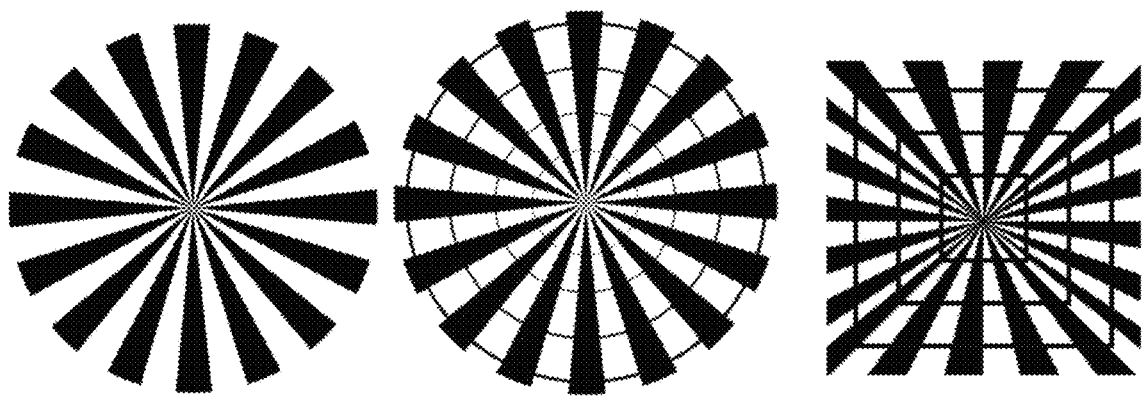

FIGURE: 4 -- Annotated Calibrated and Certified Image
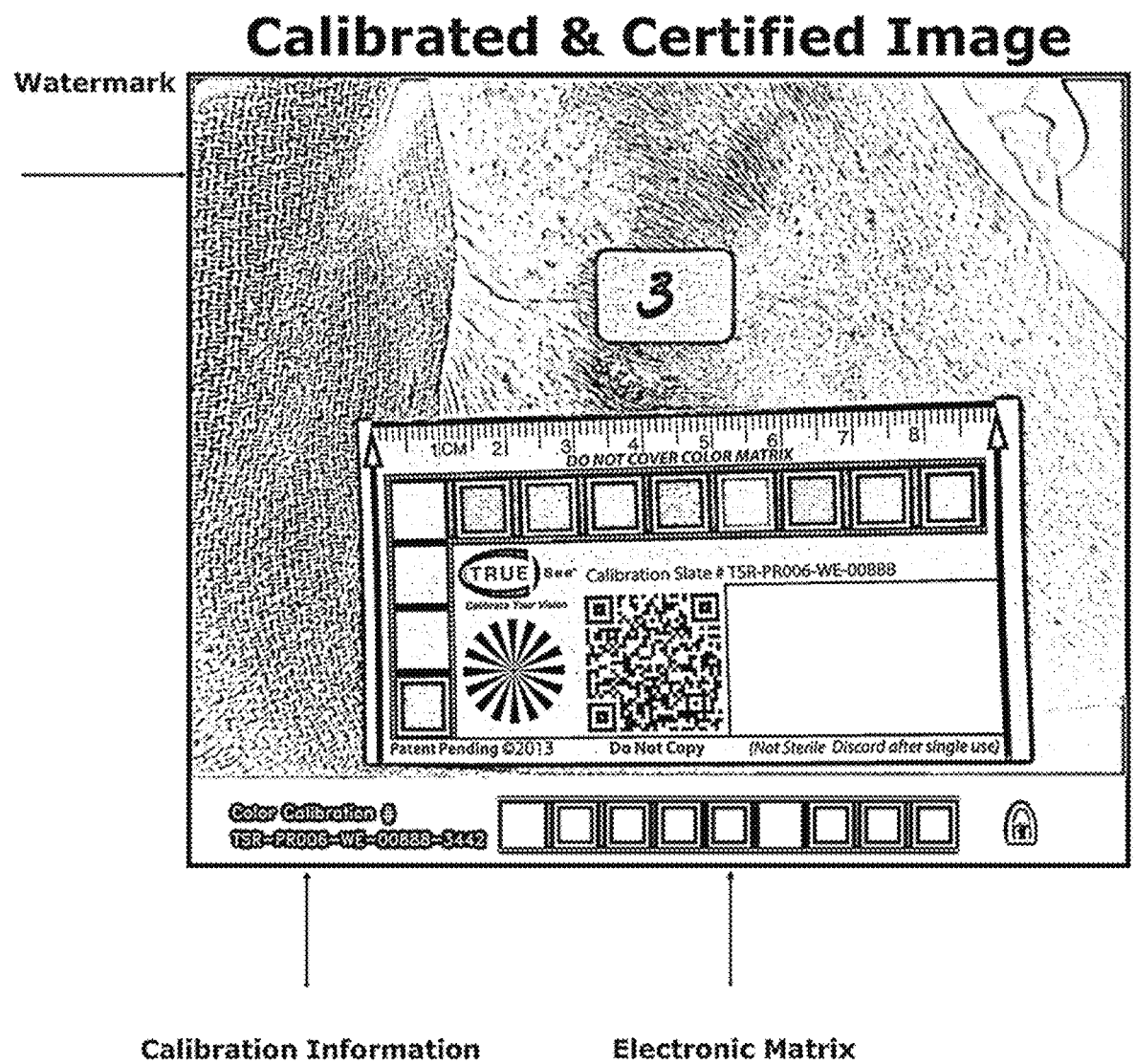

FIGURE: 5 -- Annotated SS Plug-in User Interface
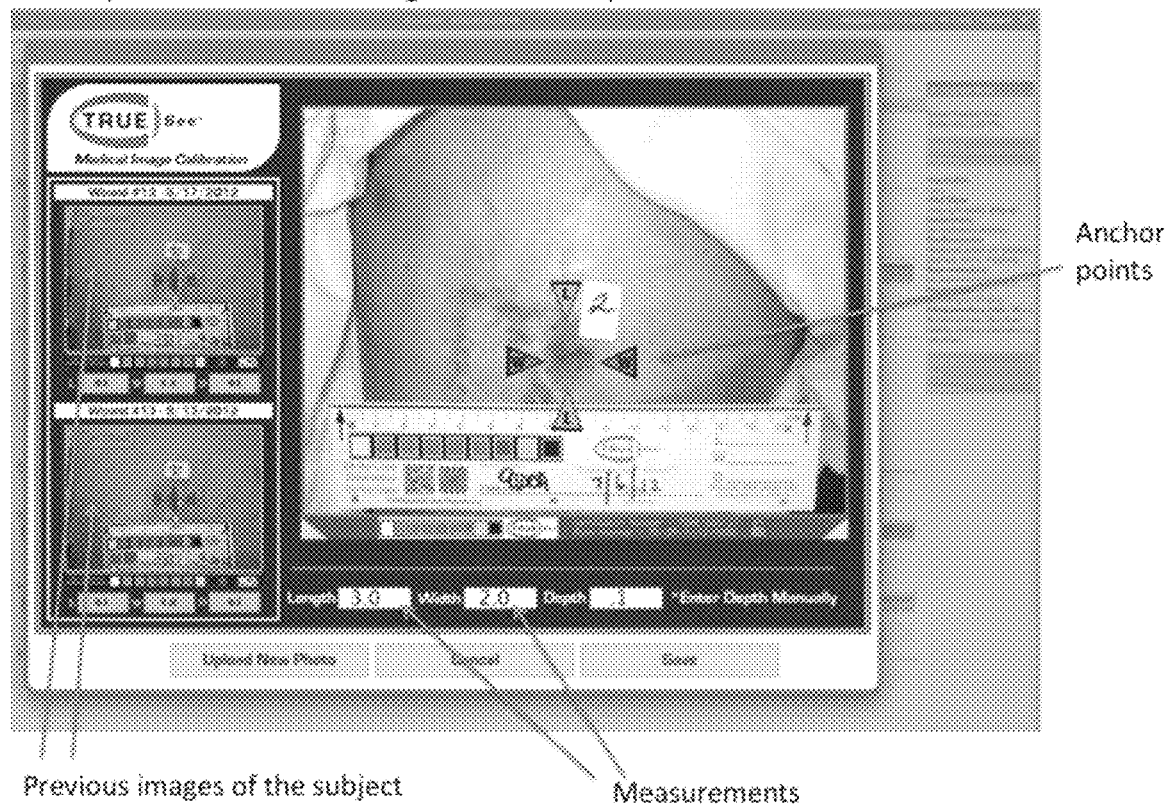

FIGURE: 6 -- Annotated User Interface Wire Frame
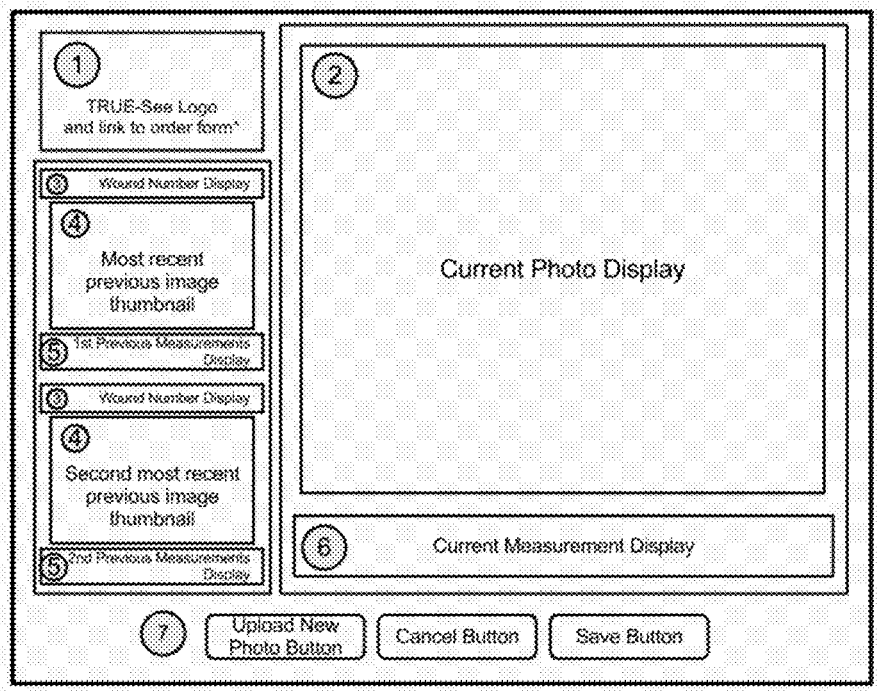
FIGURE: 6a -- Legend for Annotated User Interface Wire Frame
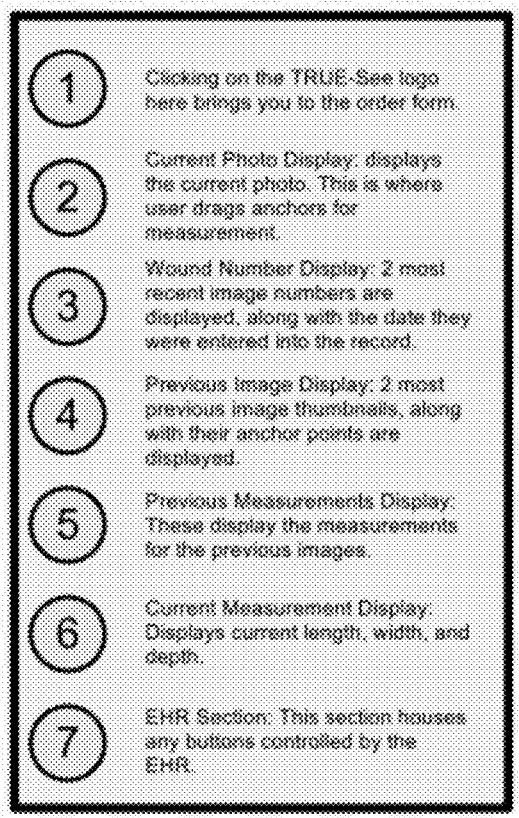

FIGURE: 7a -- Color Matrix Chart for Calibrated and Certified Picture (p.1 of 3)

Color Chart Values                                                 http://50.63.61.226/TS151_PR3/ColorChartValues.aspx

TRUE-See Universal Plug-in ( Ver 1.51, PR3)

Welcome   Home   Help

Color Matrix      Original Image      Processed Image            Settings

| Image Name | NSH-1.jpg |
|---|---|
| Natural Chips | 8 |
| Forced Natural Chips | 2 |
| Artificial Chips | No Chip Found |
| Forced Artificial Chips | No Chip Found |
| Total Chips Detected | 11 |
| Processing Status | Calibration Successful. |
| QR Code Detection Status | Detected |

| BEFORE CALIBRATION | | | | |
|---|---|---|---|---|
| Color | Red(Diff) | Green(Diff) | Blue(Diff) | Chip Find Type |
| White | 225(30) | 226(29) | 225(30) | Natural |
| Yellow | 242(13) | 212(28) | 0(0) | Natural |
| Orange | 252(-9) | 110(23) | 27(3) | Forced Natural |
| Red | 235(1) | 52(-6) | 39(-18) | Natural |
| Gray | 137(-11) | 132(-7) | 124(1) | Natural |
| Magenta | 231(4) | 44(-44) | 125(11) | Natural |

FIGURE: 7b -- Color Matrix Chart for Calibrated and Certified Picture (p.2 of 3)

Color Chart Values  http://50.63.61.226/TS151_PR3/ColorChartValues.aspx

| | | | | |
|---|---|---|---|---|
| Green | 138(-27) | 192(1) | 24(44) | Natural |
| Black | 52(-22) | 56(-29) | 55(-27) | Natural |

*Diff shows the difference from IDEAL COLOR VALUES

| CALIBRATION FACTORS | | |
|---|---|---|
| Red | Green | Blue |
| 0.919708 | 0.9469697 | 1.008065 |

| AFTER CALIBRATION | | | | |
|---|---|---|---|---|
| Color | Red(Diff) | Green(Diff) | Blue(Diff) | Chip Find Type |
| White | 207(48) | 214(41) | 227(28) | Natural |
| Yellow | 223(32) | 201(39) | 0(0) | Natural |
| Orange | 232(11) | 104(29) | 27(3) | Forced Natural |
| Red | 216(20) | 49(-3) | 39(-18) | Natural |
| Gray | 126(0) | 125(0) | 125(0) | Natural |
| Magenta | 212(23) | 41(-41) | 126(10) | Natural |
| Green | 127(-16) | 182(11) | 24(44) | Natural |
| Black | 48(-18) | 53(-26) | 55(-27) | Natural |

*Diff shows the difference from IDEAL COLOR VALUES

IDEAL COLOR VALUES

FIGURE: 7c -- Color Matrix Chart for Calibrated and Certified Picture (p.3 of 3)

Color Chart Values          http://50.63.61.226/TS151_PR3/ColorChartValues.aspx

| Color | Red | Green | Blue |
|---|---|---|---|
| White | 255 | 255 | 255 |
| Yellow | 255 | 240 | 0 |
| Orange | 243 | 133 | 30 |
| Red | 236 | 46 | 21 |
| Gray | 126 | 125 | 125 |
| Magenta | 235 | 0 | 136 |
| Green | 111 | 193 | 68 |
| Black | 30 | 27 | 28 |

FIGURE: 8 – Multiple Pictures in a Patient Record

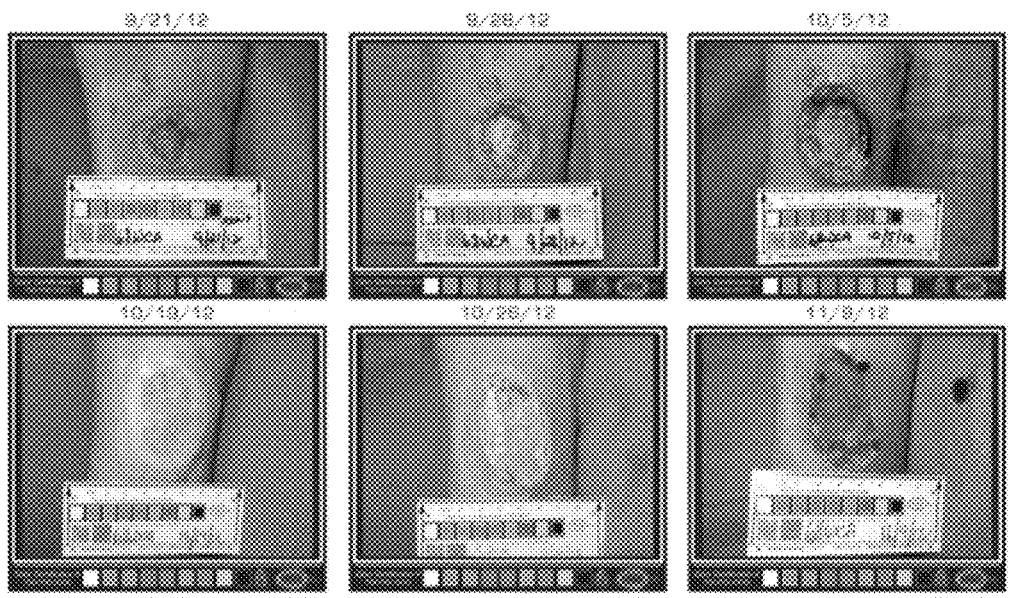

Standardized framing, Color Slate and Software System to Calibrate and Certify Image minimizes photographic variables and inconsistencies to represent variations in the subject Formula & Graph Calculating the Increment of Discernible Difference of Magenta Formula & Graph Calculating the Increment of Discernible Difference of Green FIGURE: 11 – Annotated Framing Assistance Guide with Subject
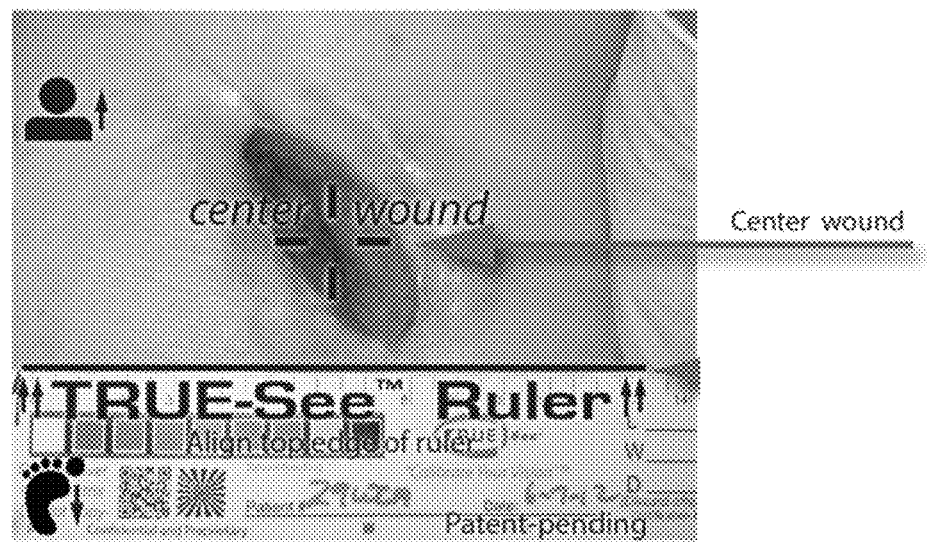
FIGURE: 12 – Etched Framing Assistance Guide on Digital Camera Screen
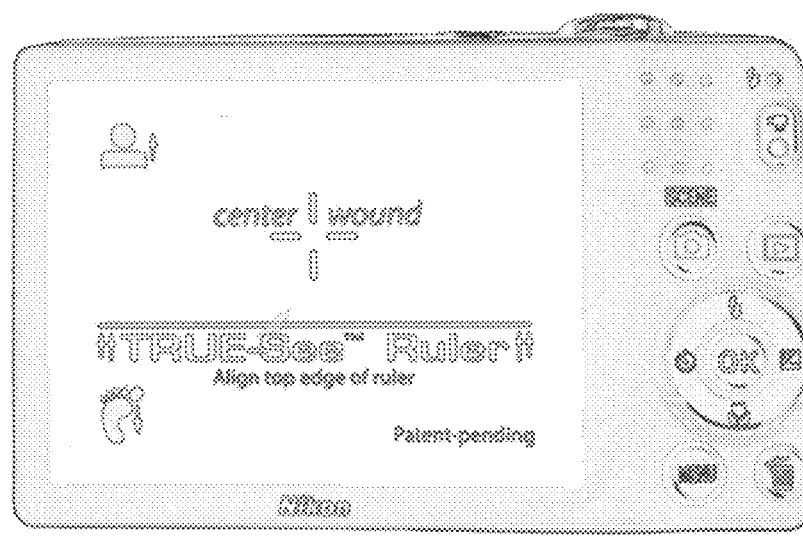

Angle Device Sample Angle Device

Annotated Side View of Angle Device on Subject with Color Calibration Slate

"Front" or "Camera" View of Angle Device on Subject with Color Calibration Slate

Wound Label Device (two alternate versions)

Annotated Wound Label Device on Subject with Calibration Slate

Annotated Wound Label Device on Subject with Calibration Slate

FIGURE 15: -- System Software Deployment Charts
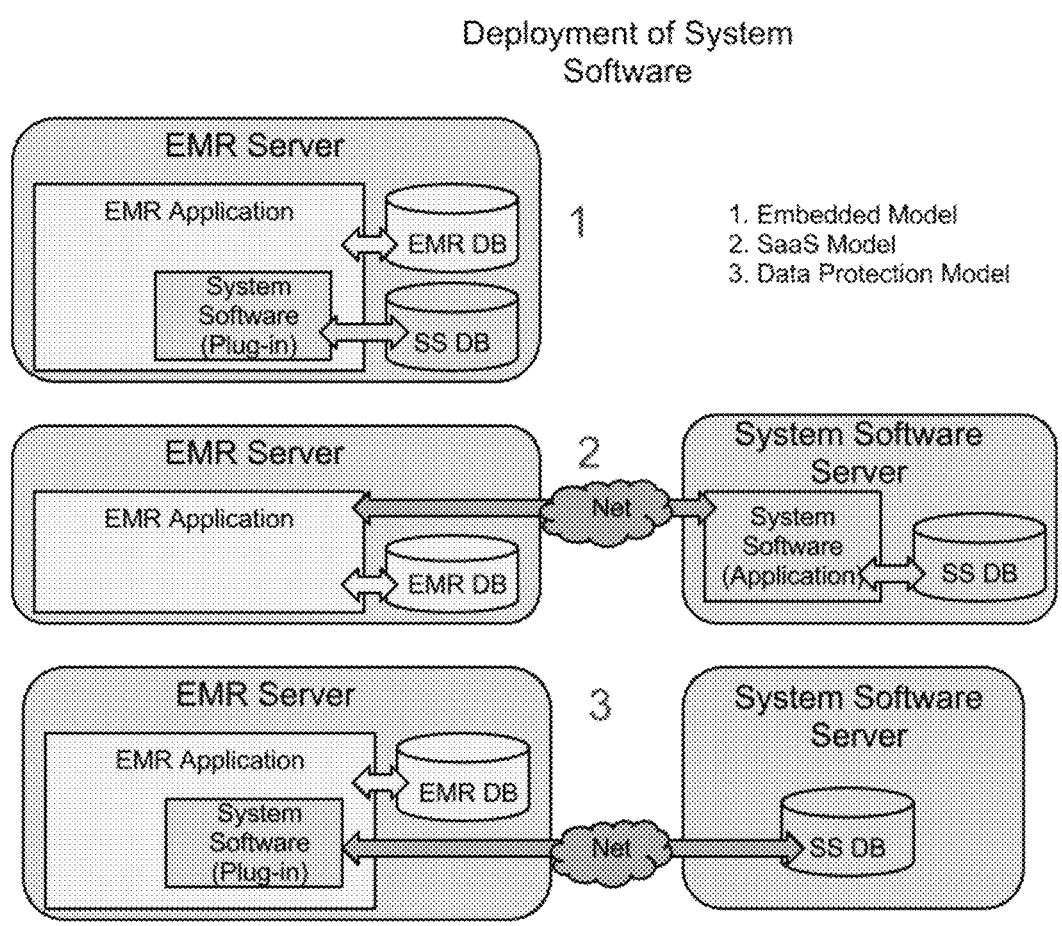

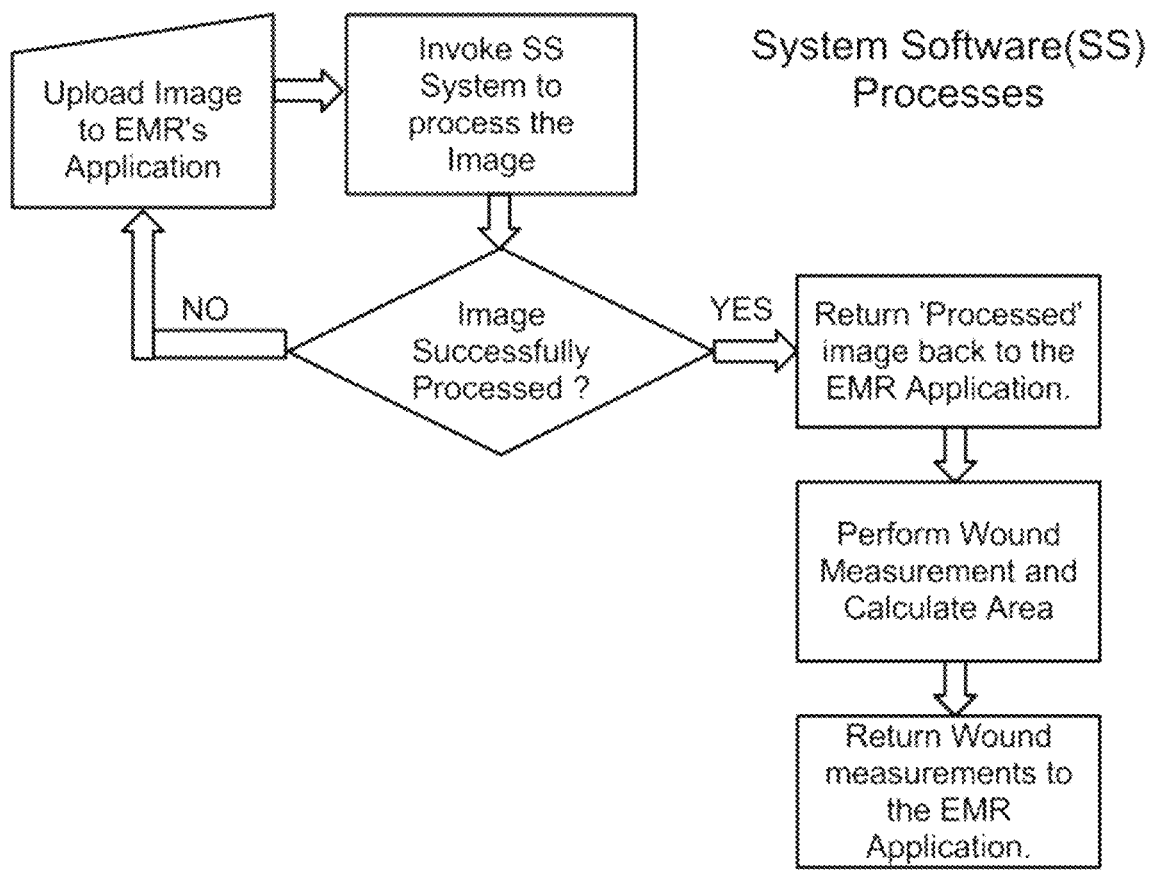
FIGURE 16: -- System Software Processes Charts

FIGURE 17: -- System Software Interfaces Chart
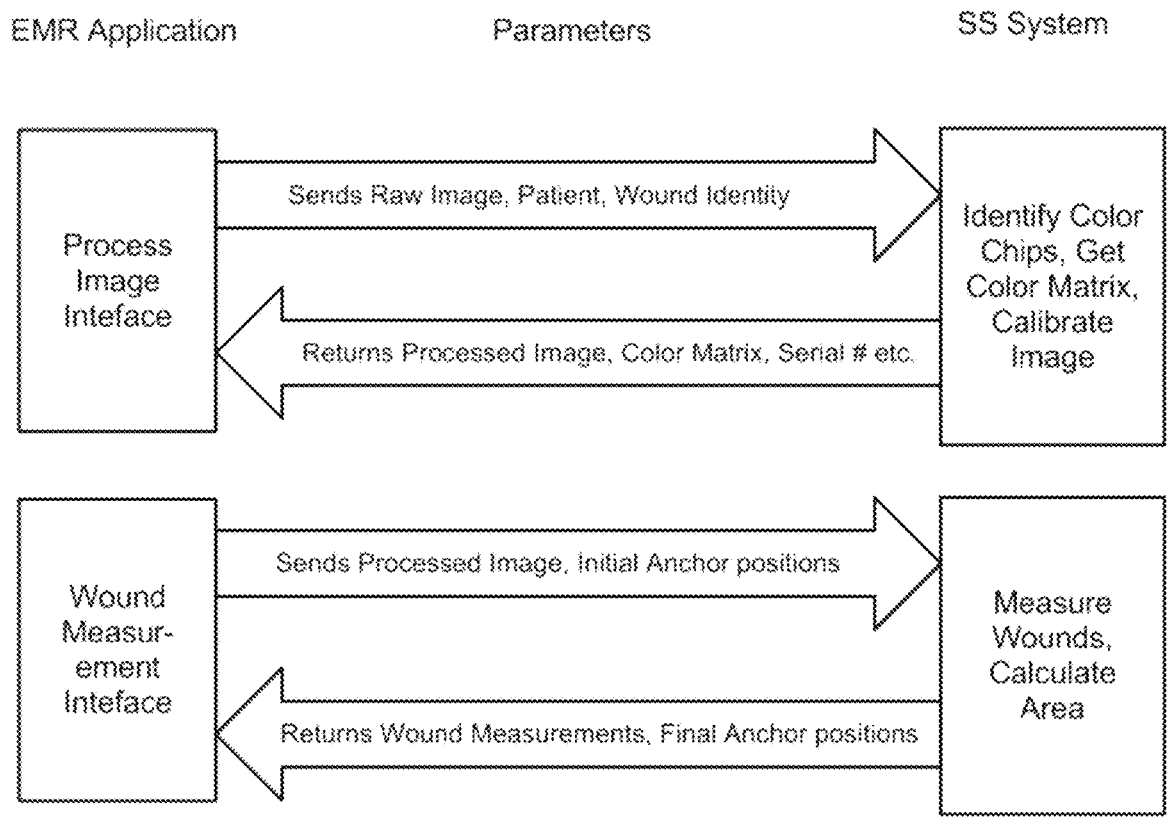

FIGURE 18: -- Mobile Device Cloud Based System Software Implementation Diagram
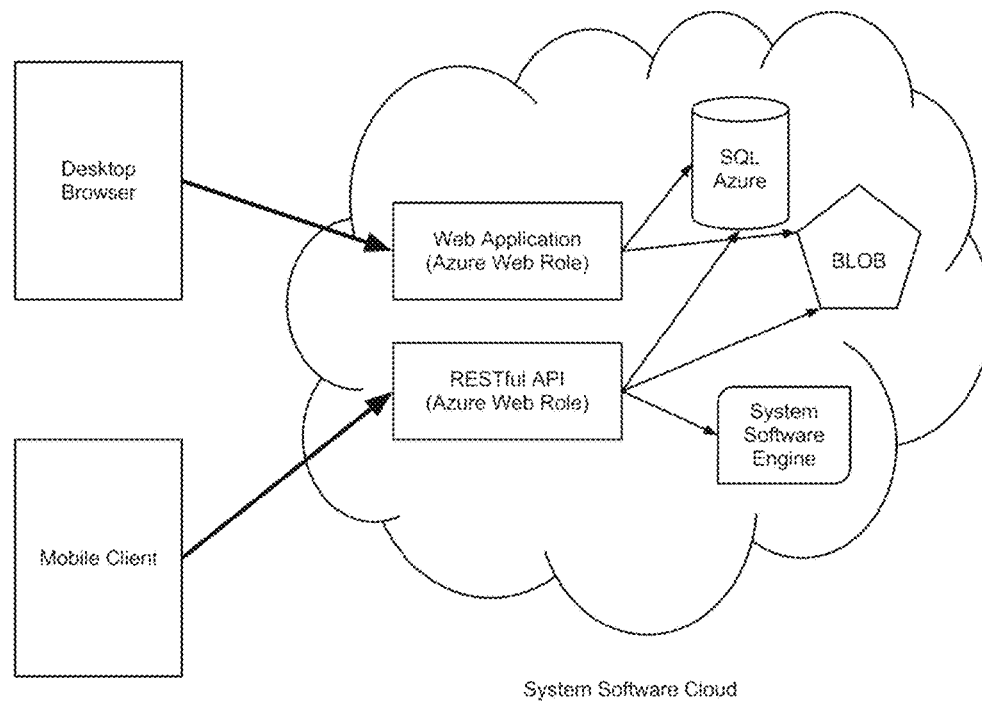

FIGURE 19: -- Protocols and Instructions for Image Capture Process

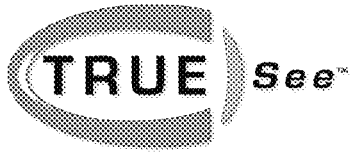

Instructions

The following steps will help you make the most of your TRUE-See™ System components.

Step one:
Check to make sure the settings of your TRUE-See™ System Camera are correct. See insert or www.true-see.com for correct settings. Note: the camera will arrive with correct settings.
    Select the following items from the shooting menu:
        8 megapixels
        Auto white balance
        Color options: Vivid

Step two:
Remove the protective strip from the adhesive on the back of the TRUE-See™ Calibration Slate. Place the TRUE-See™ Calibration Slate on the surface of the skin, just below the wound.

NOTE: The head of the patient should be above the top of the frame, and the foot of the patient should be below the bottom of the frame. This is indicated in the upper and lower left sides of the TRUE-See™ Framing Assistance, which is either engraved on the LCD screen of your TRUE-See™ System Camera, or applied as a decal.

NOTE: For wounds that are on the end of a body part, such as a toe or heel where there is no skin surface to adhere to, use the TRUE-See 90° Angles to attach the slate on the same plane, below the wound.

Step three:
Using the TRUE-See™ Framing Assistance, center the wound where indicated, and align the top edge of the TRUE-See™ Calibration Slate with the line as indicated. DO NOT ZOOM in or out. Back the camera away as necessary to include the entire Slate, edge to edge, as well as the wound.

Step four:
Take the picture.

Step five:
After you take the first picture, look to see if the colors in the photo look like the colors on the TRUE-See™ Slate in front of you. If the colors do not look correct, please check the camera settings before continuing. Repeat these steps until an acceptable image is obtained.

Step six:
Upload your pictures into WoundExpert®, or into whichever electronic medical record keeping software you use.

Tips:
-Remember to keep the TRUE-See Slate flat against the skin, and align it so that it is straight on the line in the TRUE-See Framing Assistance.

-Take 3-5 pictures, and pick the best one later.

-TRUE-See™ Calibration Slates are non-sterile and disposable. Discard after single use. Do not use a Slate on more than one patient or on more than one visit.

Copy Protected • Keep out of light • Store in cool, dark space • Each Slate is Unique

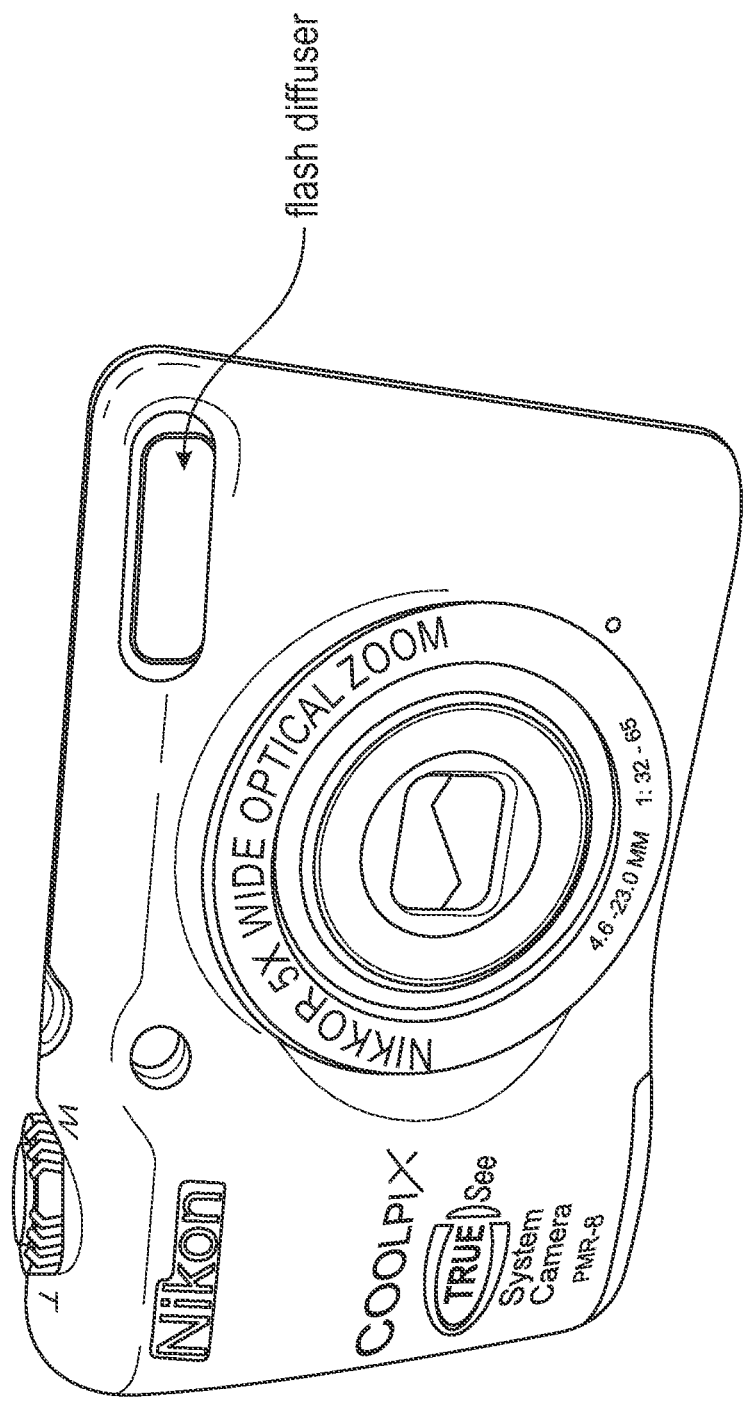

SYSTEM FOR PRODUCING CONSISTENT MEDICAL IMAGE DATA THAT IS VERIFIABLY CORRECT

CROSS-REFERENCE TO RELATED APPLICATIONS

Priority of U.S. provisional patent application No. 61/799,843, filed 15 Mar. 2013, incorporated herein by reference, is hereby claimed.

U.S. provisional patent application No. 61/646,678, filed 14 May 2012, is incorporated herein by reference. U.S. patent application Ser. No. 13/105,758, filed 11 May 2011, is incorporated herein by reference. U.S. provisional patent application No. 61/333,620, filed 11 May 2010, is incorporated herein by reference. This is not a continuation or continuation-in-part of any prior patent application.

STATEMENT REGARDING FEDERALLY SPONSORED RESEARCH OR DEVELOPMENT

Not applicable

REFERENCE TO A "MICROFICHE APPENDIX"

Not applicable

DESCRIPTION

The TRUE-SEE System

ALL RIGHTS RESERVED

The TRUE-SEE System
"Because Seeing is Believing" or "Believe What You See"
"Calibrate your Vision" "Confidence, Quality and Consistence"
TRUE-SEE is a trademark name that has been filed for a US Trademark

BACKGROUND OF THE INVENTION

1. Field of Invention

This invention relates generally to the photographs, video and visual media in medical related fields such as, but not limited, to human and animal medical trials, treatments, veterinary medicine, and forensics.

2. General Background

Studies have shown some of the advantages of color correction and color accuracy through use of standard color devices or charts however these do not provide a cost effective, commercial means to achieve this.

There are similar devices on the market, but most are expensive and cumbersome. For example, Aranz Medical has a product called the Silhouette, which is an expensive device that measures wound volume, using lasers. Similarly, WoundZoom has an expensive camera element, which forces users to align a set of lasers on the plane of the subject, in order to perform planary measurements. These both exemplify some of the limitations of the current state of medical photography. These products provide little help for a clinician who is already having trouble using a standard camera to obtain pictures. Nurses and clinicians are further burdened by these new and confusing pieces of technology. We designed our system to seamlessly adapt to current workflows, utilizing elements that are already commonplace and widely used.

The American Telemedicine Association and other organizations have specific guidelines for many aspects of the current uses, however none have color & luminance standards for the image let alone the other helpful aspects of the TRUE-SEE System. There is currently nothing on the market that is offering the solutions of this application that the inventor is aware of.

The following U.S. Patent Documents are related:

| | | |
|---|---|---|
| 4,811,084 | March 1989 | Belmares-Sarabia et al. |
| 4,763,186 | August 1988 | Belmares-Sarabia et al. |
| 4,866,511 | September 1989 | Belmares-Sarabia et al. |
| 4,914,506 | April 1990 | Kafer et al. |
| 5,874,988 | February 1999 | Xueming |
| 5,912,720 | June 1999 | Berger et al. |
| 5,987,519 | November 1999 | Peifer et al. |
| 6,033,076 | March 2000 | Braeuning et al. |
| 6,610,010 B2 | August 2003 | Sjöqvist |
| 6,757,010 B2 | June 2004 | Fasciano |
| 20060256129 | November 2006 | Xu et al. |
| 7,290,893 | November 2007 | Amphlett |
| 7,428,324 B2 | September 2008 | Crandall et al. |
| 7,372,481 B2 | May 2008 | Tomita |
| 7,688,231 | March 2010 | Rotenstein |

For more information, please see the following References:

Bala, Raja et al., IEEE Transactions On Image Processing, Vol. 14, "Two-Dimensional Transforms for Device Color Correction and Calibration," pp. 1172-1186, 2005.

Chanussot-Deprez, Caroline et al., International Wound Journal, Vol. 5, "Telemedicine in wound care," pp. 651-654, 2008.

Cukierski, William J. et al., Proc IEEE International Symposium Biomed Imaging, "Moving Beyond Color: The Case For Multispectral Imaging In Brightfield Pathology," pp. 1-11, 2009.

Matveev, Nikolay V. et al., Journal of Telemedicine and Telecare, Vol. 12, "Automatic colour correction of digital skin images in teledermatology," pp. 62-63, 2006.

Münzenmayer, Christian et al., IEEE Transactions On Biomedical Engineering, Vol. 53, "A Spectral Color Correction Framework for Medical Applications," pp. 254-265, 2006.

Oakley, John P. et al., IEEE Transactions On Image Processing, Vol. 16, "Correction of Simple Contrast Loss in Color Images," pp. 511-522, 2007.

Oduncu, Hakan et al., The International Journal of Lower Extremity Wounds, Vol. 3, "Analysis of Skin Wound Images Using Digital Color Image Processing: A Preliminary Communication," pp. 151-156, 2004.

Parara, Sofia M. et al., Proceedings of the 11th WSEAS International Conference on COMPUTERS, "Digital Image Analysis for the comparative study of skin erythema after skin closure of surgical wounds," pp. 409-413, 2007.

Tachakra, Sapal et al., Journal of Telemedicine and Telecare, Vol. 5, "Colour perception in telemedicine," pp. 211-219, 1999.

Tachakra, Sapal et al., Journal of Telemedicine and Telecare, Vol. 6, "A comparison of telemedicine with face-to-face consultations for trauma management," pp. 178-181, 2000.

Treuillet, Sylvie et al., IEEE Transactions On Medical Imaging, Vol. 28, "Three-Dimensional Assessment of Skin Wounds Using a Standard Digital Camera," pp. 752-762, 2009.

Van Geel, Nanny et al., Eur J Dermatol, "A new digital image analysis system useful for surface assessment of vitiligo lesions in transplantation studies," pp. 150-155, 2004.

Van Poucke, Sven et al., BMC Medical Imaging, Vol 10, "Automatic colorimetric calibration of human wounds," pp. 1-11, 2010.

Van Poucke, Sven et al., International Wound Journal, Vol 7, "Comparative analysis of two methods for wound bed area measurement," pp. 366-377, 2010.

Vander Haeghen, Yves et al., Arch Dermatol, Vol 142, "Consistent Cutaneous Imaging With Commercial Digital Cameras," pp. 42-46, 2006.

Wang, Xingzheng et al., IEEE Transactions On Information Technology In Biomedicine, Vol. 14, "An Optimized Tongue Image Color Correction Scheme," pp. 1355-1364, 2010.

Wang, Zhi-Guo et al., IEEE Transactions on Consumer Electronics, Vol. 55, "A Method of Dynamic Skin Color Correction Applied to Display Devices," pp. 967-972, 2009.

Wannous, Hazem et al., IEEE Transactions On Medical Imaging, Vol. 30, "Enhanced Assessment of the Wound-Healing Process by Accurate Multiview Tissue Classification," pp. 315-326, 2011.

BRIEF SUMMARY OF THE INVENTION

There are many advantages to the invention as described herein especially in the medical related fields. In summary, many of them pertain to means of mass production, ease of use and marketability to produce commercially viable means for the objectives set forth.

BRIEF DESCRIPTION OF THE DRAWINGS

FIG. 1a—Sample Calibration Slate 1a
FIG. 1b—Sample Calibration Slate 1b
FIG. 1c—Sample Calibration Slate 1c
FIG. 1d—Sample Calibration Slate 1d
FIG. 2—Annotated Calibration Slate
FIG. 3—Examples of Focus Charts
FIG. 4—Annotated Calibrated and Certified Image
FIG. 5—Annotated SS Plug-in User Interface
FIG. 6—Annotated User Interface Wire Frame
FIG. 6a—Legend for Annotated User Interface Wire Frame
FIG. 7a—Color Matrix Chart for Calibrated and Certified Picture (p.1 of 3)
FIG. 7b—Color Matrix Chart for Calibrated and Certified Picture (p.2 of 3)
FIG. 7c—Color Matrix Chart for Calibrated and Certified Picture (p.3 of 3)
FIG. 8—Multiple Pictures in a Patient Record
FIG. 9a—Formula & graph calculating the Increment of Discernible Difference of Black
FIG. 9b—Formula & graph calculating the Increment of Discernible Difference of Gray
FIG. 9c—Formula & graph calculating the Increment of Discernible Difference of White
FIG. 9d—Formula & graph calculating the Increment of Discernible Difference of Yellow
FIG. 9e—Formula & graph calculating the Increment of Discernible Difference of Orange
FIG. 9f—Formula & graph calculating the Increment of Discernible Difference of Red
FIG. 9g—Formula & graph calculating the Increment of Discernible Difference of Magenta
FIG. 9h—Formula & graph calculating the Increment of Discernible Difference of Green
FIG. 9i—Formula & graph calculating the Increment of Discernible Difference in Cyan
FIG. 10—Framing Assistance Guide
FIG. 11—Annotated Framing Assistance Guide with Subject
FIG. 12—Etched Framing Assistance Guide on Digital Camera Screen
FIG. 13a—Angle Device Sample
FIG. 13b—Annotated Side View of Angle Device on Subject with Color Calibration Slate
FIG. 13C—"Front" or "Camera" View of Angle Device on Subject with Color Calibration Slate
FIGS. 14a-b:—Wound Label Device (two alternate versions)
FIG. 14c—Annotated Wound Label Device on Subject with Calibration Slate
FIG. 14d—Annotated Wound Label Device on Subject with Calibration Slate
FIG. 15—System Software Deployment Charts
FIG. 16—System Software Processes Charts
FIG. 17—System Software Interfaces Chart
FIG. 18—Mobile Device Cloud Based System Software Implementation Diagram
FIG. 19—Protocols and Instructions for Image Capture Process
FIG. 20—Front of Camera Showing Flash Diffuser

DETAILED DESCRIPTION OF THE INVENTION

Figure 9A:
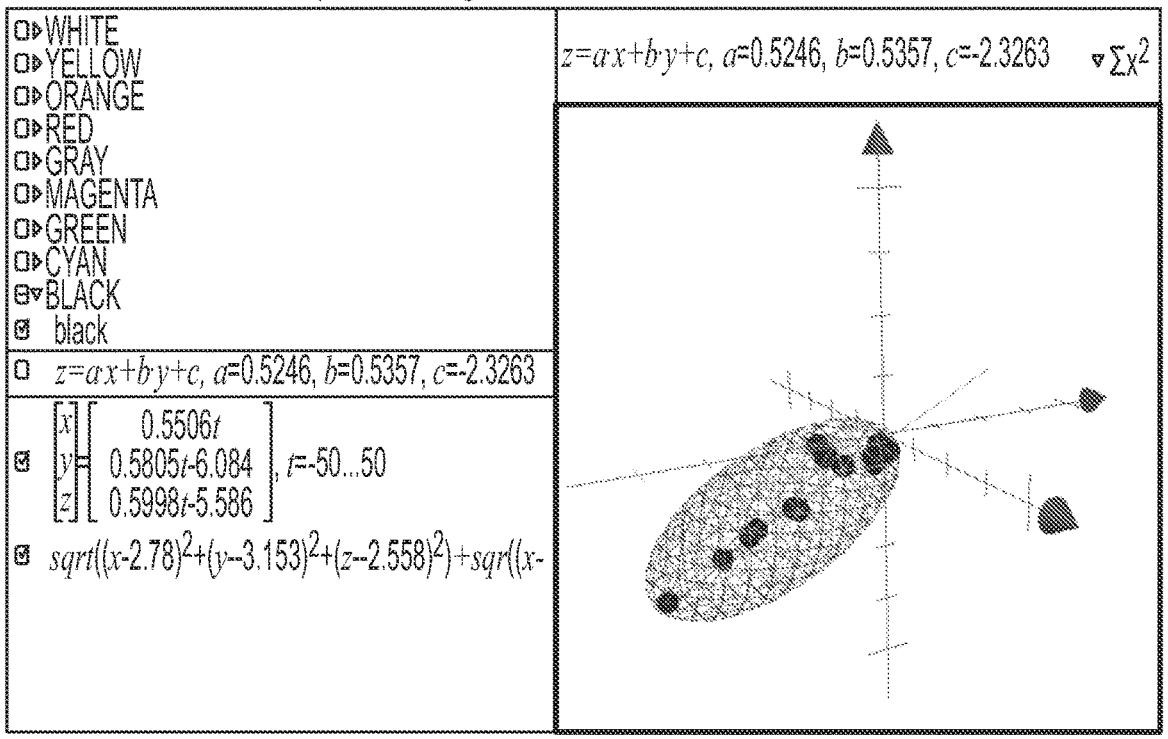
Figure 9B:
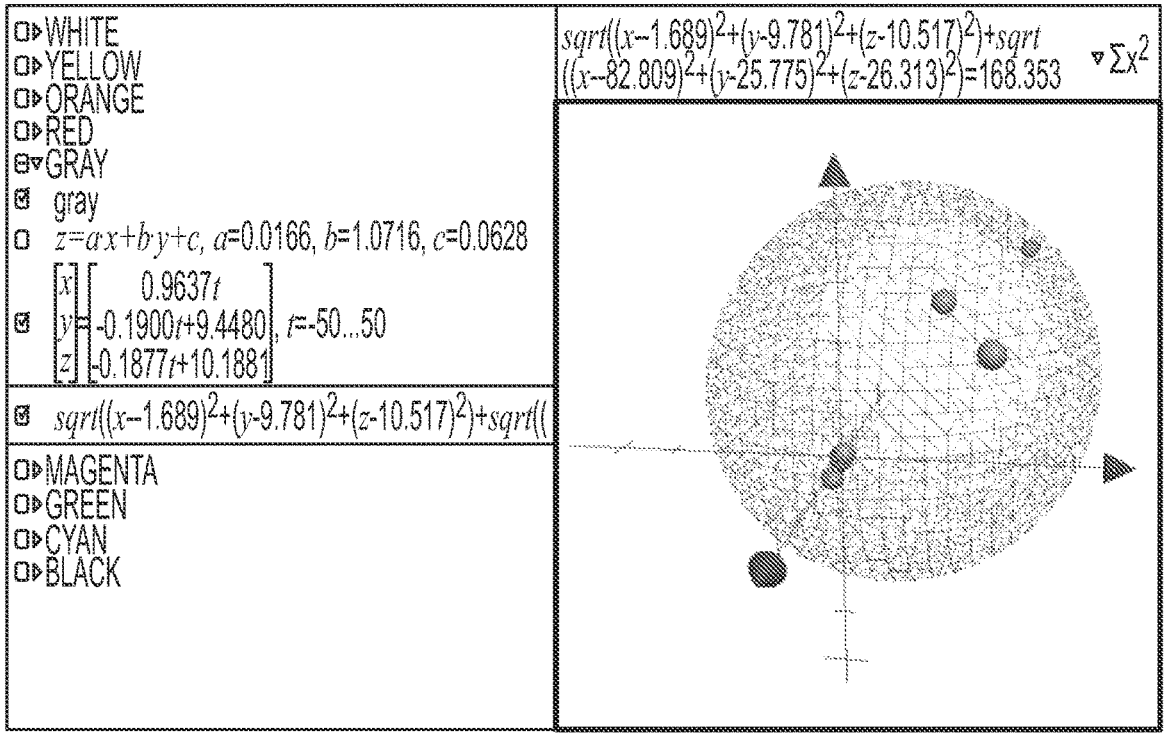
Figure 9C:
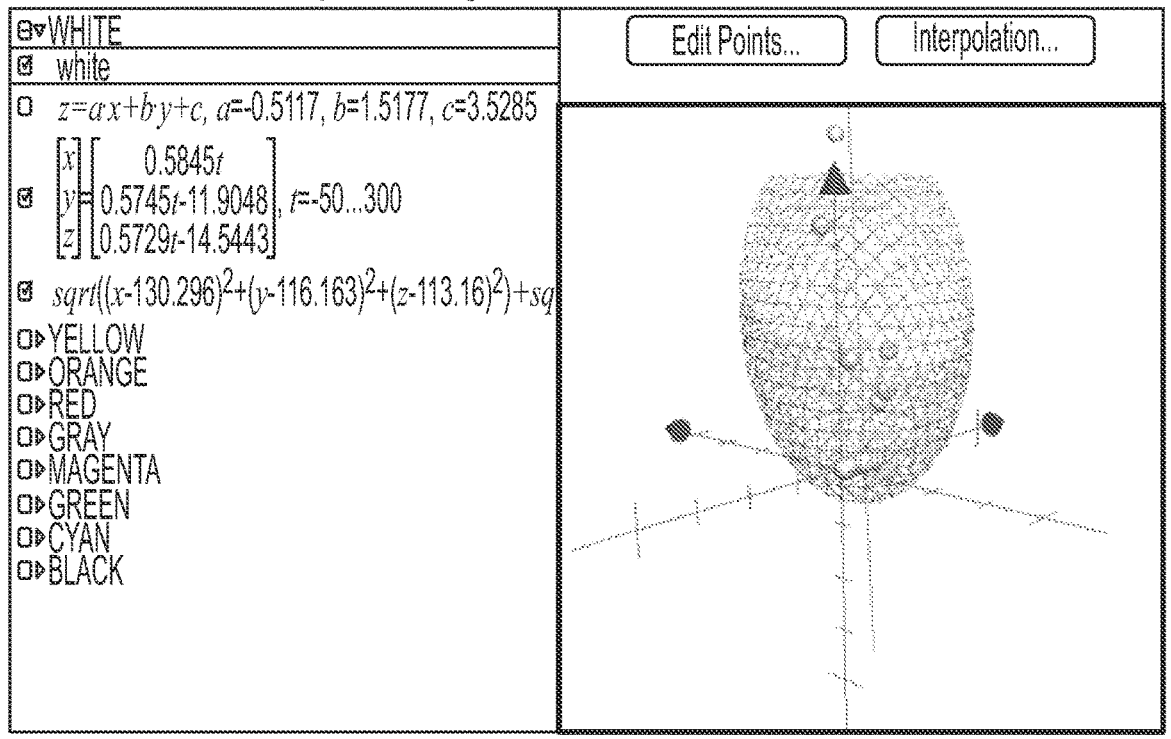
Figure 9D:
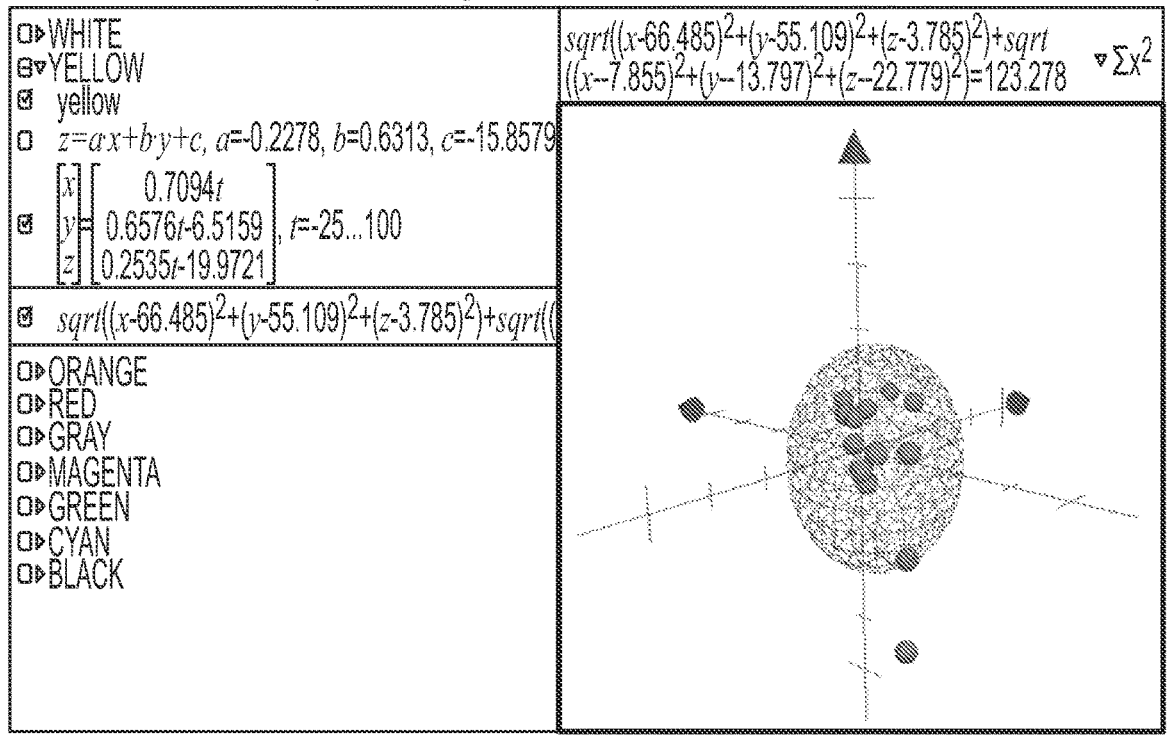
Figure 9E:
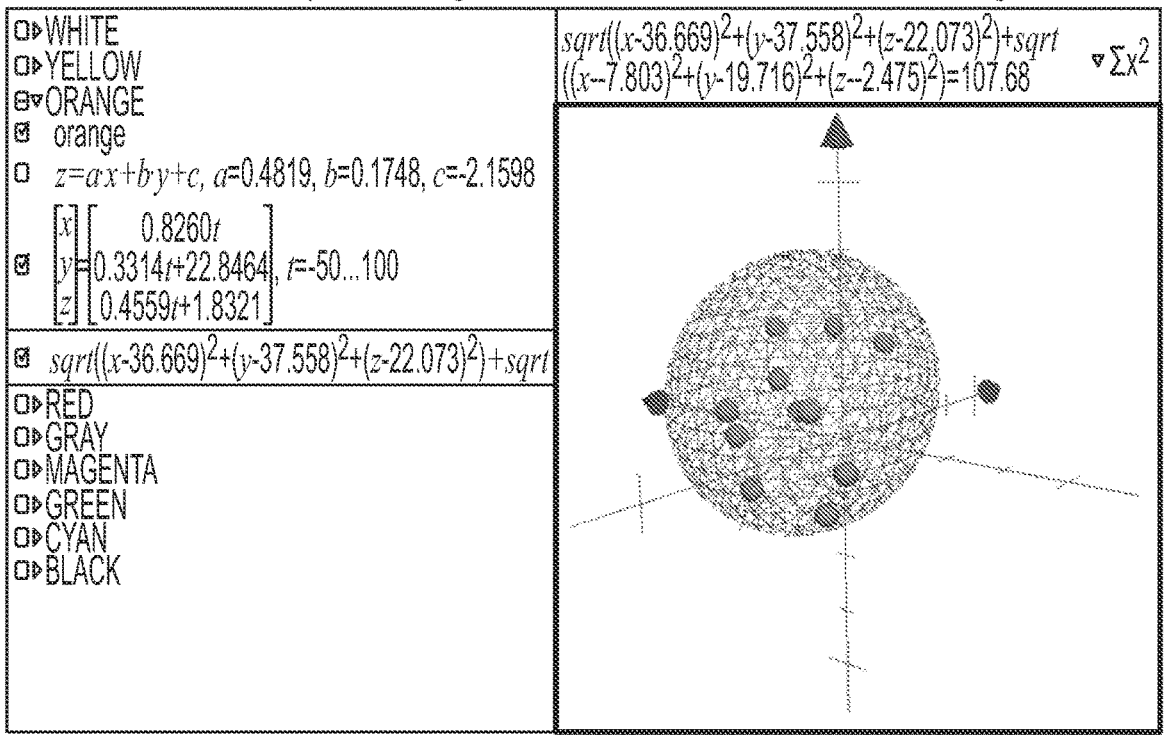
Figure 9F:
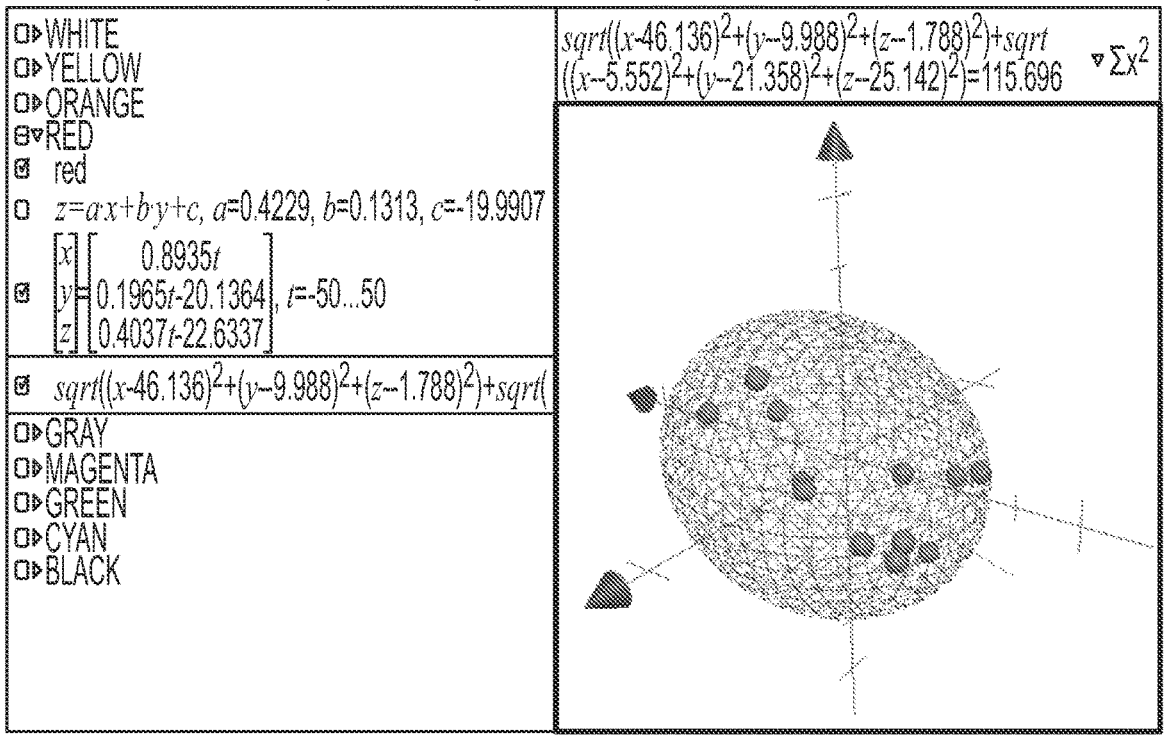
Figure 9G:
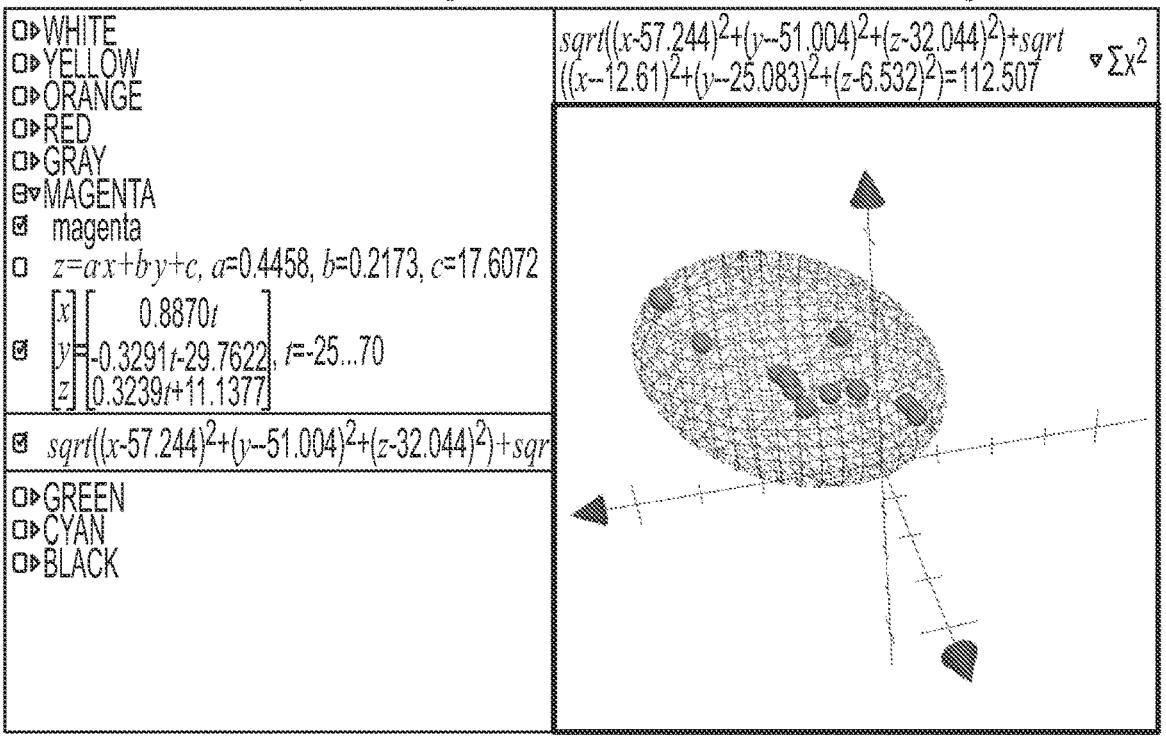
Figure 9H:
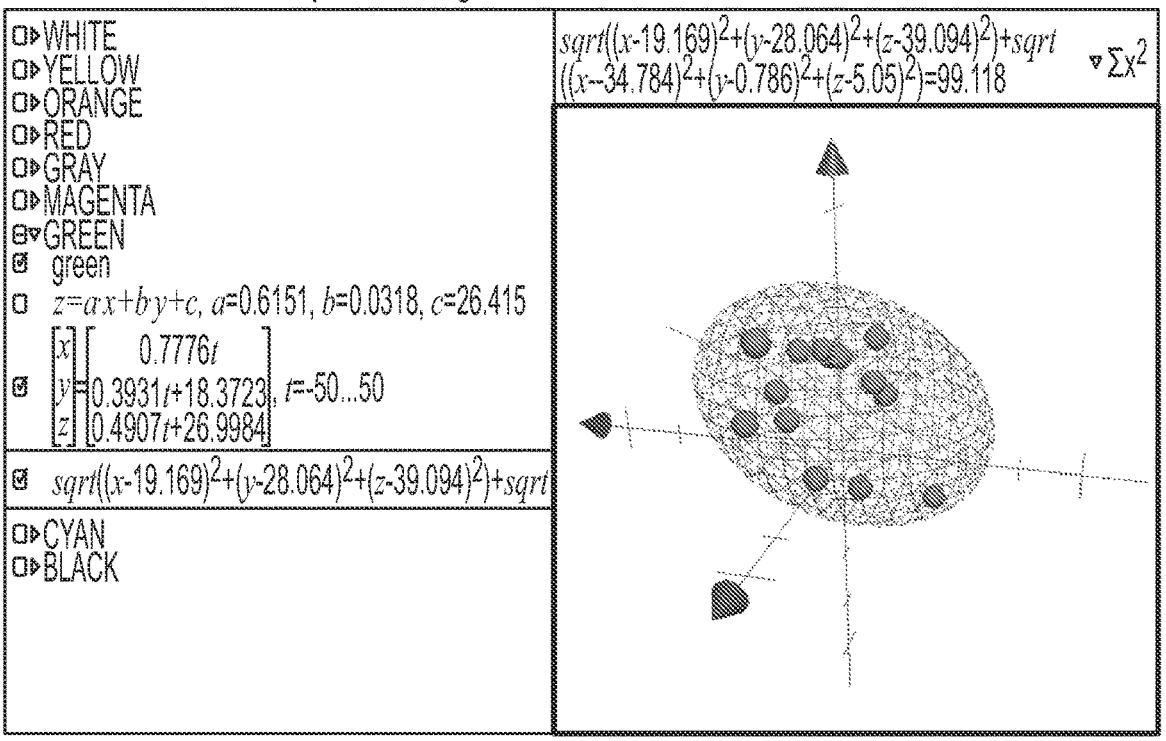
Figure 9I:
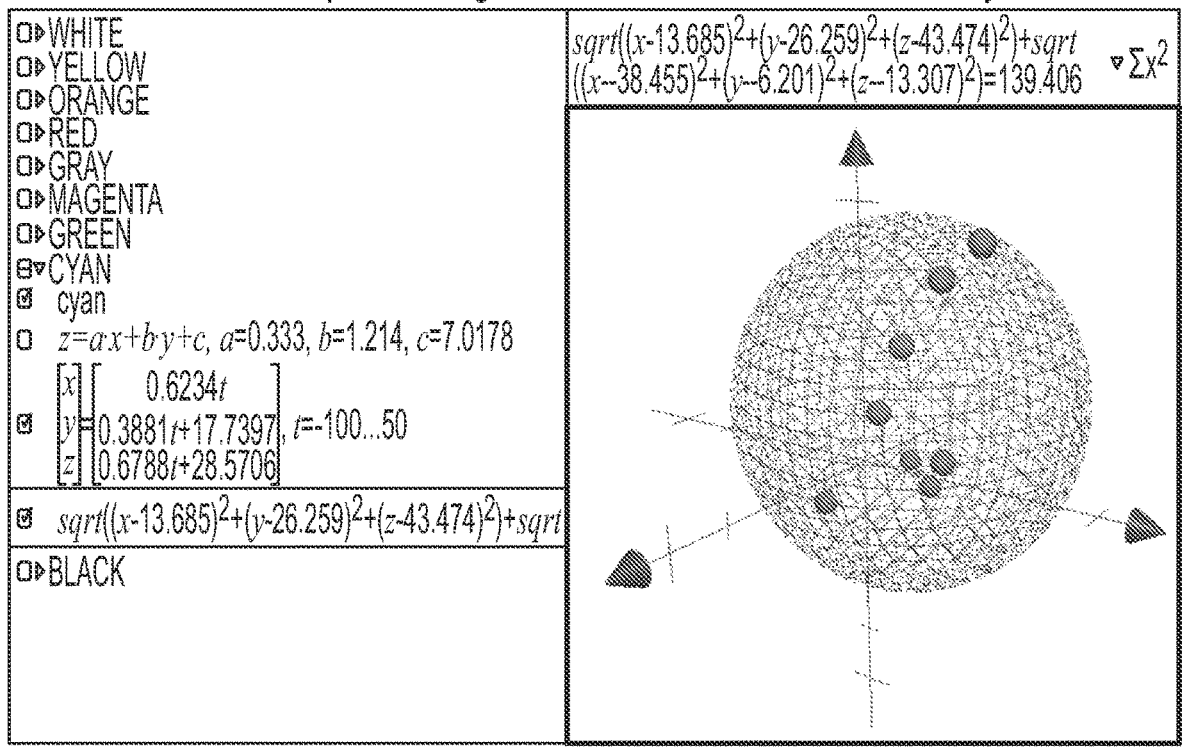

FIGS. 1a-d and 2 show an iteration of the calibration slate, as it would be used in the field. It may contain, but is not limited to, a color set or color matrix designed along multiple axes for digital calibration and skew detection, parallel lines/arrows for further skew detection and alignment assistance, a unique QR code, a unique slate number, a debridement status check box, etc.

FIG. 2 shows an Annotated Calibration Slate. The slate preferably includes a focus chart, skew analysis configuration of squares/figures, a unique identifying number for print run, and slate and in QR form, a color set or color matrix, guidance arrows (see opposite side of slate as well), and measurement markings. Alternatively, the measurement markings may be omitted or minimized. Preferably, the color matrix includes the following colors in order from right to left: white, yellow, orange, red, grey, green, magenta, cyan, and black.

FIG. 4 shows a sample Annotated Calibrated and Certified Image. This image preferably includes a unique number indicating certification as shown in FIG. 4. The calibration strip in the image preferably includes images to subjectively and objectively (with System Software) verify focus. The image preferably includes visible and invisible security features. Additionally, the reshaped picture profile is preferably immediately identifiable. Preferably, the calibrated and certified image includes a printed color set (on the calibration slate) and an electronic color set as shown in FIG. 4. The image also preferably includes visible and invisible watermarks.

FIGS. 5-6a show the user interface as it would appear as an EMR/EHR plug-in. Section (1) displays the software logo, and preferably provides a link to order more slates. Section (2) of the user interface displays the "current image", and allows the user to set measurement parameters using the provided anchor points. Sections (3) display the wound number and date entered into record for the previous image thumbnail that displays directly below it. Sections (4) display thumbnails, along with measurement anchor points, of previous images obtained for the wound and patient that are the subject of the current image. The actual length, width and depth associated with each thumbnail are displayed in Sections (5), directly below the thumbnail. As with Sections (5), Section (6) displays length, width, and depth for the current image, and is displayed directly below the current image. Section (7) is a space reserved for buttons whose functionality is directly controlled by the host EHR.

FIG. 5 shows a sample user interface in the plug-in version of the System Software. As shown in FIG. 5, the sample EMR is preferably shown in the background. Also shown in FIG. 5, the anchor points preferably indicate the length and width positioned by a user. The user interface preferably includes previous images of the subject with their anchor positions and measurements. The measurements are generated by the System Software preferably using the anchor system.

Figure 10:
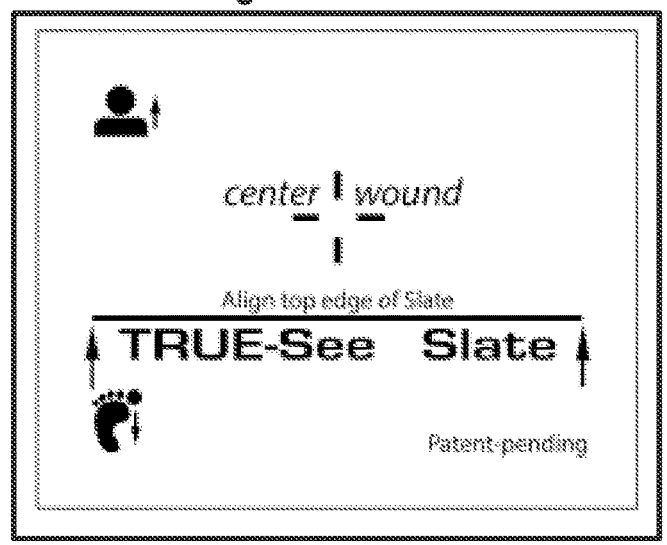

FIGS. 10-12 show the framing assistance guide as it would appear on the user's image capture device. The horizontal line through the middle, along with the two arrows that point to it, are used for alignment of the slate. The cross hair in the center is used for centering the subject to be photographed. The head image at the top left, and the foot image on the bottom left are used to ensure proper anatomical orientation of the subject being photographed. The subject's head should always be oriented toward the top, and the subject's foot should always be oriented toward the bottom of the frame.

FIG. 11 shows an Annotated Framing Assistance Guide with Subject including the head of the patient oriented to the top of the image and the foot of the patient oriented to the bottom of the image. As show in FIG. 11, the top of the ruler is preferably aligned to the line on the framing assistance guide.

Figure 13A:
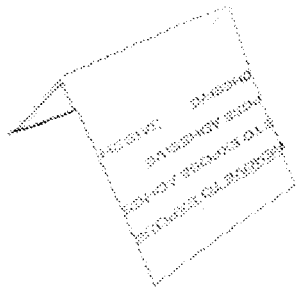
Figure 13B:
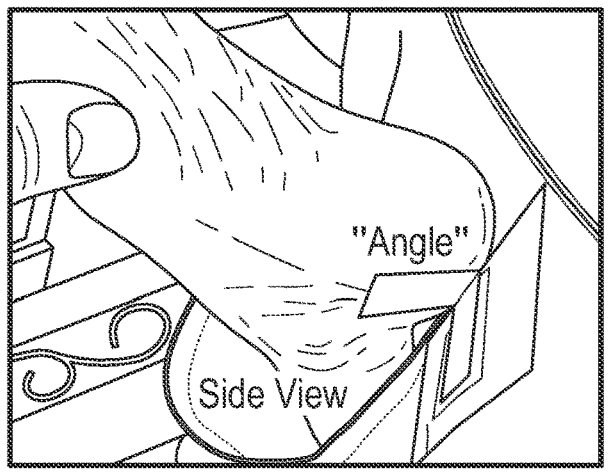
Figure 13C:
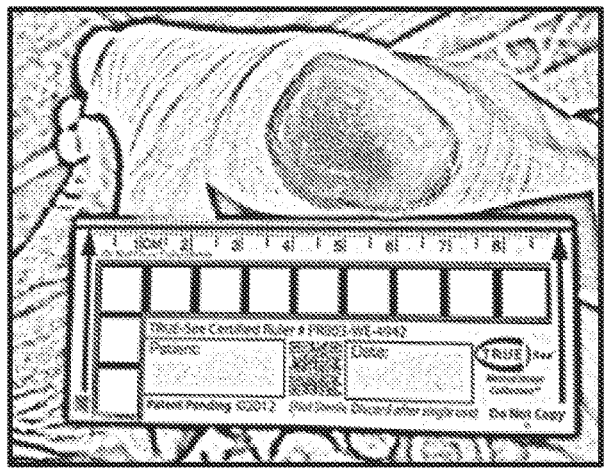

FIGS. 13a-c show the scored 90° angle card, as well as how to use it as a peripheral to the calibration Slate. The card is scored in the middle, and has an adhesive strip on one or both of the outside tabs. This allows the user to mount a slate on the same plane as the wound, even when there is insufficient skin surface below the subject. It is folded at a 90° angle at the center, scored section, and applied to the back side of the slate, with the adhesive facing upward. This will allow the user to mount the slate to fingertips, toes, amputation sites, etc.

Figure 14A:
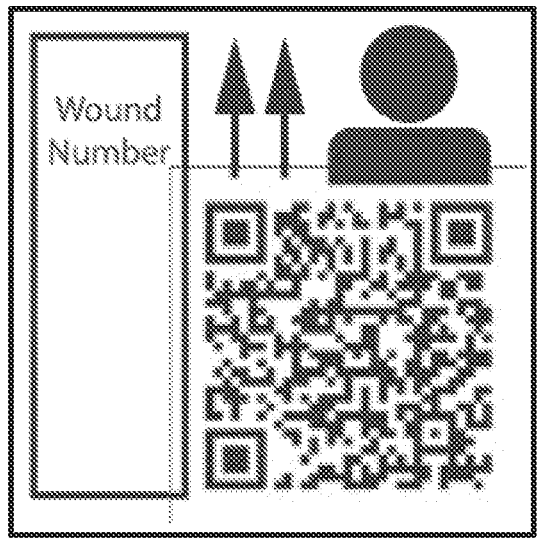
Figure 14B:
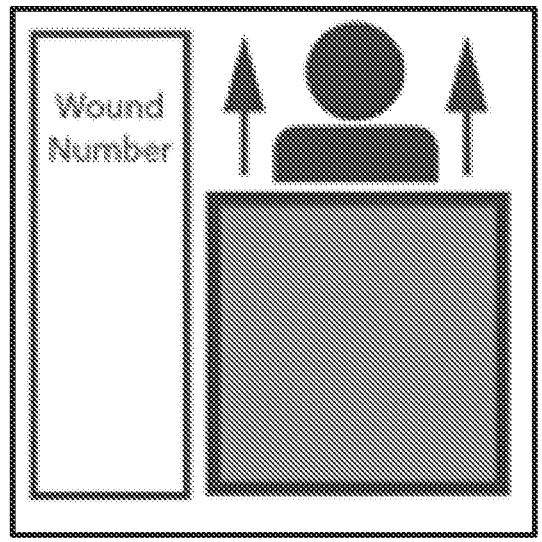
Figure 14C:
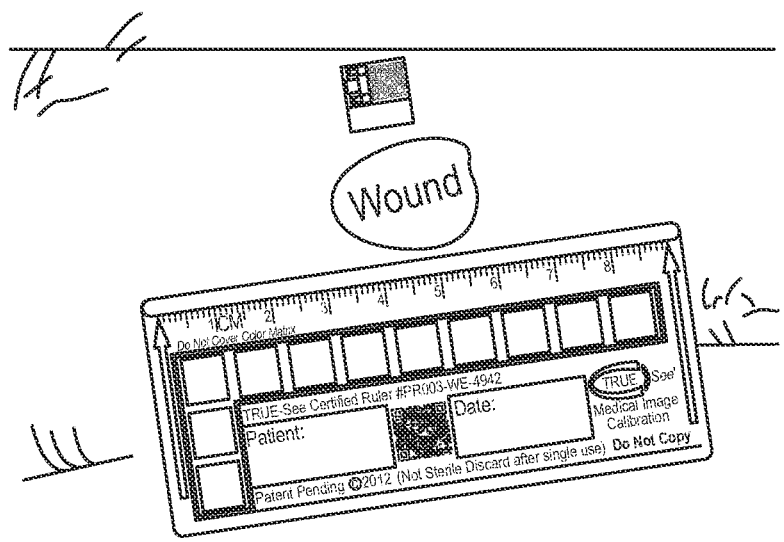
Figure 14D:
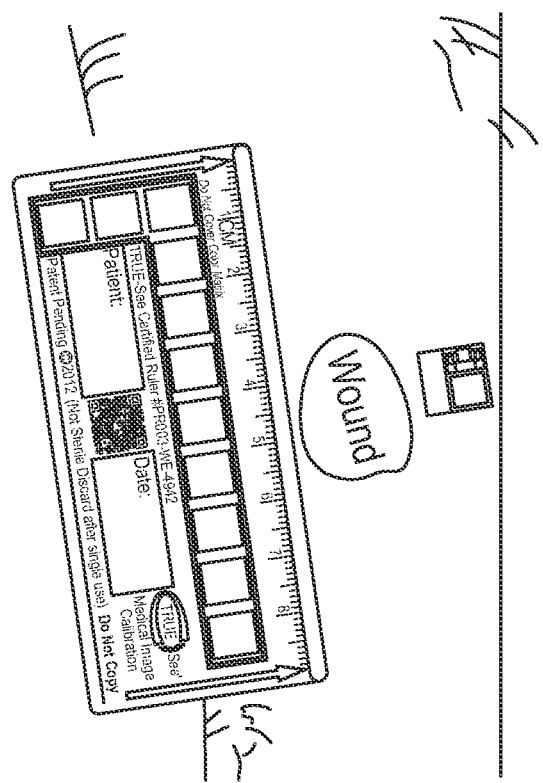

FIGS. 14c and 14d show an Annotated Wound Label Device on a Subject with Calibration Slate. The device includes a wound label and a calibration slate. The wound label is placed to identify the head of the patient so that the System Software can auto-rotate the image so the "head" of the patient is at the top of the picture as shown in FIG. 14d.

FIG. 20 shows the front of a Camera Showing Flash Diffuser. The camera preferably has a Professional-grade flash diffuser that equalizes lighting in the pictures. The camera preferably includes serial numbers that are engraved on the front to prevent cameras from walking away.

The invention may apply not just to visible light, but also to all forms of electromagnetic radiation. Similarly invention pertains not just to current known electronic means of reproducing and displaying reality, but also to others known and unknown.

By example in this document we refer to RGB values to describe color however other color spaces with similarly corresponding components would also work.

A system for producing consistent medical image data that is verifiably correct that includes a consistent or inconsistent light source; a consistent or inconsistent image recording device; a disposable calibration slate which appears in at least one image recorded by the image recording device.

The system for producing consistent medical image data that is verifiably correct wherein the image recording device may or may not include a lens, and the light source surrounds the lens of the image recording device.

Lighting protocols which may include a diffused flash on the image capture device, room lighting protocols, or some similar method of lighting.

An image capture device, which may or may not record and store information regarding the distance from the capture device to the subject being photographed.

A framing assistance guide, which assists users in aligning key elements of the photograph, 5 resulting in consistent framing for medical records.

A flash diffusion device which may be applied directly to the flash, or at some distance between the flash and subject, which softens and spreads light evenly throughout the photograph.

A disposable calibration slate which may include a color and/or density chart for calibration of an image which includes the calibration slate.

A calibration slate which may include a color and/or density chart for calibration of an image which includes the calibration slate, wherein The color and/or density chart is matched to a new standard for each printing run by means of tracking the chart by printing run.

A calibration slate which may include a means of quantifying focus by means of concentric shapes that are read by software.

A disposable calibration slate which may have a numbering system such that each slate is unique (and this is printed in a form such as a variable QR code so that a software can read that number.)

A disposable calibration slate that may have identifying features such as squares or QR codes arranged in two or more axis (such as x & Y) on the slate to provide a means of reading the skew of the slate relative to the picture-taking device.

A disposable calibration slate which is included in at least one image, and contains a color chart and ruler or similar measuring device.

A color set printed on various sized materials so that it can captured in any recording device including microscopic.

A disposable calibration slate which may include medical information such as patient info, location, physician ID, and/or similar data.

Combining color slate with elements of existing wound rulers such as but not measuring elements such as marks at centimeter and/or millimeter to facilitate measuring.

Making a color set or slate that is disposable so it can be placed on/near the wound without contamination which may or may not have an identifying element.

A means of producing printed color sets with consistent color using CMYK colors in their purest form, thereby creating spot colors.

So that when the slate is photographed, it can be indentified and matched to the color values of each color or element in the color set element of that slate.

A means of displaying the printing color set in a picture in proximity to the matching standard color set, electronically or otherwise.

A means of combining the printing color set in a picture in proximity to the matching standard color set, electronically or otherwise.

A means of printing color sets in CMYK color space, and translating them into an electronic color space for comparison on a computer monitor, mobile device, or similar display.

A means by which the electronic color values obtained from the printed color sets are converted into numeric targets and visual representations.

A means of displaying pictures containing a printed color set alongside an electronic color set in close proximity to one another for qualitative comparison.

A means of tracking and matching print runs of a particular color set with their corresponding electronic values and electronically displayed color set.

A Wound Label Device with identifying features such as squares or QR codes that may be adhered to the skin adjacent the subject providing a means of calculating relative distance and skew.

A disposable, angled, adhesive-backed device for mounting wound rulers, charts, or similar device, at a 90° angle to skin, fabric, or any other surface to be photographed.

A mobile application, which facilitates correct framing and orientation, utilizing hands free image capture capabilities.

A system of quantifying color differences among colors, and certifying that the colors are a visual match.

A system software capable of reading elements within a photograph, mapping them, using known sizes to generate the number of pixels per mm, cm, inch, etc., and using that mapping to generate measurements from within the software.

Means of calibrating the color in an image by identifying the grey in the color set in a picture, reading the value of this color and then calculating the difference or delta from the known target of that grey before it was reproduced and/or captured such as in a photograph. Then applying adjusting the entire image by the difference to bring the grey back to or close to the target known value of that grey. This will then shift all colors in that picture and thus "correct" them to the standard of the grey.

Similarly, a System Software can calculate the difference or delta from the target for any color including white and black to calculate the correction back to each target of each color.

A proprietary formula for calculating the numeric combinations of Red, Green, and Blue for each color in a color set, and determining all color mixtures that produce a visual match to that color.

A means of calculating the numeric combinations of Red, Green, and Blue for each color in a color set, and determining all color mixtures that produce a visual match to that color using the elements of the color such as but not limited to R, G, B as axes to plot the delta in from the target where the target is expressed in the intersection (or zero point) of all three elements.

And the delta from the target is used to plot the position of each color in relation to the axes of elements.

And the positions of each color as plotted is then analyzed to decide whether it lies within a range from the intersection or zero point.

And that shape of the range from the zero point in the axes is described as an ellipsis or ellipsoidal shape.

And where there this a formula to describe mathematically the "sum distance from the foci or zero point".

And where this is used to filter the acceptable distance from the target expressed by the zero point.

And thus have a numeric means of determining the acceptable range of color from the target.

And thus providing a numeric means to translate the range of visible difference between any color in a color set as defined by a group of views.

A method of placing multiple points of interest on the surface of skin to generate information regarding skew, angle, curvature, and similar three-dimensional anomalies, and correct for them in a system.

The Wound Label Device(s) in combination with a System Software is therefore a method and means of:

(1) numbering the wound in a means readable to a software (2) indicating orientation in a means readable to a software (3) providing a means of having the software automatically orient the picture (assuming the user has placed the Wound Label Device properly)

(4) calculating scale in the picture by a software (5) calculating relative distance from the other elements such as a Calibration Slate, additional Wound Label Device or other elements (by a software) in the picture (6) using known sizes and positions of the elements on the Would Label (such as but not limited to QR code or boxes) to calculate skew base on how far off the different sides/parts of the element are from their known proportions and sizes, (7) using the known value of the elements compared to how these elements are represented in the photograph to identify, analyze and/or calculate the curvature of the subject that the Wound Label is adhered to (8) providing a means to triangulate or otherwise mathematically map the differences such as but not limited scale, skew between the relative position of the Wound Label and other data points provided in the picture such as but not limited the color set or calibration slate (9) identifying the plane of the wound relative to plane defined by the Calibration Slate or similar device

(10) indentifying, analyzing and/or calculating the difference in the plane of the subject versus that of the Calibration Slate (if any)

(11) calculating the accuracy of planary measurements based on how accurately the plane of the Calibration Slate is representing the plane of the actual wound or subject and/or

(12) indentifying, analyzing and/or calculating the curvature of the actual wound or subject All of the methods above can be used separately or in any combination.

Part 1: Method and Device for Evaluating Color and Image Quality in Medical Related Pictures.

See FIGS. 1a-d & 2

Provide a printed set of colors, which may include, but is not limited to, black, white, grey (preferably at 50-70% grey, expressed as % between white and black) and/or various other colors. This printed set is placed in the picture with the subject as it is taken. This will hereafter be referred to as the "color set."

The color set can be printed on various materials such as but not limited to some form of plastic, paper, card stock with or without and adhesive backing such as but not limited to an adhesive strip or entire backing of adhesive.

Alternatively, the color set could be on an electronic device such as a "KINDLE" or smart phone or pad, however the accuracy of the rendition of the color set in the environment preferably matches the environment and characteristics of the subject. I.e., if the subject is a physical object lighted by reflected light, the color set preferably is a physical object lighted by same reflected light in the same conditions and/or environment and captured by the same device so that the same light and condition effect the color set or Slate and the subject. The color set in any form that can serve same function may herein be referred to as Calibration Slate or Slate.

A Calibration Slate preferably would have other elements in addition to the color set.

The slates would preferably be printed on a sturdy, heavyweight, paper, card stock, or similar material with the dullest coating possible such as "dull" aqueous coating over the color set. This is done to minimize glare and maximize color saturation. Glare and color saturation issues also be minimized with a flash diffuser (FIG. 20). The diffuser would preferably be mounted directly to the flash, but may also fall anywhere in between the flash and the subject being photographed.

Typically, paper or similar rulers are only intended for single use and are discarded after each use. Calibration Slates are NOT a sterile item and should NOT be used in a sterile surgical field. Preferably, Slates should not be stored in direct sunlight or be exposed to excessive heat.

The terms "print, print run, printing etc., are referring generically to a process of embodying the color set in a physical form, or a form which is subject to the same physical environmental conditions as the subject being captured.

Preferably, a color set is embodied in a physical form, or a form that is subject to the same physical and environmental conditions as the subject being captured. Preferably, the capture device captures the image of the subject, with the color set visible in it, with the same conditions affecting the color set and the subject. Preferably, the color set is then translated into the appropriate color space for display. (herein often referred to as the "electronic color set, or slate, or calibration slate) (see other section that discusses color space, most often generically referred to as RGB for ease in this document, but not limited to RGB color space.)

Preferably, there is an indentifying element or mechanism on the "printed slate" such as, but not limited to, numbers, letters, combination of both, or other means of demarcating the slate.

Preferably, this indentifying element or mechanism can be read by a software or the System software. The identifying element can be, but is not limited to, QR codes or bar codes, and can be read by the software using Optical Character Recognition, Open CV, or some other means of reading the demarcation.

Preferably, the demarcation provides a means of matching match the "printed slate" to a corresponding "electronic" version of that slate.

Preferably, the System software would store the demarcating element of the "printed ruler" and the "electronic" version of the slate.

Thus the System software or similar device provides a means to display, or provide the elements for display, for the "printed" version of the slate with the corresponding "electronic" version of that slate, in close proximity to each other, and would preferably be displayed together. This is important because it provides the user or viewer a means of seeing and judging the correlation of the elements of the color set or slate, to determine how closely they match each other.

Similarly, numeric means to read, calculate and set thresholds of acceptability are possible and preferably are used as well. See Calibration and Certification sections.

Thus, by providing a known or control (the printed slate) in the picture, subject to the same environmental, technical and behavioral (picture taking methods or protocols—See FIG. 19) variables as the patient or subject, and providing a corresponding known in the appropriate color space of the desired display, this invention may provide means to subjectively indentify and judge the qualities of the picture. This can be extremely important and valuable in medical related fields. (In addition, "medical related fields" is defined elsewhere in this document, but the intent is to also refer to fields such as, but not limited to, veterinary, forensic, dermatology, and all fields related to testing, study, treatment, and assessment in the medical field.)

Alternately, the slate and angle could be sterile and appropriately packaged. Alternately, the slate dimensions could be printed or reproduced on very small scale, to be used in microscopic pictures, or pictures of very small subjects, such as may be the case in dermatology or other fields.

Alternately, the slate may be printed on plastic, vinyl, coated metal, or some other suitable material that can be cleaned and sanitized for medical applications.

The values of each color in the color set are measured for both print and electronic color spaces.

The color set is placed in the frame with the subject. The color set should be on the same plane as the wound, and the same light should be falling on it.

A picture is preferably taken with both the subject and the color set clearly visible in the frame. Preferably, the user would follow a set of protocols, including but not limited to the set of protocols shown in FIG. 19. This may include standard image capture settings, framing guidelines, and/or other protocols to help obtain clear images for processing. FIG. 19 is the preferred embodiment of the protocols, but the actual set may vary. Preferably, the user would receive a printed copy of these protocols with all orders. Printed slates are only intended for single use, and should be discarded after use.

For electronic media to display the correct electronic version of the color set, use a colorimeter, spectrophotometer, or similar device to read the values of the printed color set, and convert them to an electronic color space such as RGB, CIElab, or similar. (Since the first iteration was built using RGB, the color space will hereafter be referred to as RGB). Using the electronic color value readings of each color, construct an electronic color set with the values that match the printed color set. The electronic, matching version of the color set is created using graphic software, such as PHOTOSHOP.

The color set creates a control in every image so that the same scientific method used in all other aspects of medicine, can be utilized to calibrate medical related imagery.

Thus, the color set is a means of empirically documenting, measuring and correcting medical related imagery, by establishing a control, which establishes a standard for care that currently does not exist in this way. (Without which there is no standard.)

It should be noted that industry standard or common elements on the color chart allow for unmeasured, but qualitatively significant, color correction by most $3^{rd}$ party color correction software. Thus, it is a tool in itself, outside the TRUE-SEE System, as well as within it. If one uses an inexpensive reproduction of the colors and grey scale, they likely will not have the correct target values. Red may not reflect the correct red on a color meter. However, if it is metered, and the offset from the true value is known and consistent, the red in that chart can be used as a target in reproduction to evaluate correctness because it is a known representation. Thus, one could do a printing of wound rulers that is not perfectly in adherence with the specifications of the target colors and still use them as the target in this process to obtain correctness and variance because once the offset of each printing is known, it can be part of the calculation.

Means of Providing this on a Mass, Affordable Scale. See FIGS. 1a-d & 2

Preferably, the printing process is controlled so that the printing of the color sets is consistent within each printing (or print run). This can be achieved by utilizing CMYK colors in their pure form, to create inexpensive spot colors, and use the minimum number of Pantone® colors possible. Preferably, the printer may randomly pull color sets throughout the printing, ensuring that the colors have remained consistent. If the variance is unacceptable, the batch is rejected. If the variance is acceptable, the RGB values of that batch become the new target, or norm.

(Ex: pull and designate color sets from the beginning, middle and end of the print run.) Analyze for variation, and establish whether or not the variance throughout the printing constitutes a statistically negligible value. Establish that consistency is acceptable by several means of quality controls known and devised such as but not limited to ISO 9000, best practices by standard to the printing industry, writing up a quality control method to check spot check randomly items of the printing as described above.

Placing a known, measured color chart in the image, in the same conditions as the subject, allows for qualitative and quantitative empirical comparison between the physical reality of the subject, and the electronic reproduction of that reality. Without this means of calibrating the image, one has no empirical means of judging the image, because there is no control in the process. This tool creates a standard of care that is measurable and consistent. Without such a tool and process, there is no standard of care or scientific means of measuring the correctness of images being used in medical applications.

Preferably, print identifiers on the color sets indicate the print run. This may be a unique identifier on each color set, or some similar identifier on the physical slate. This can provide means to match color sets from multiple different printings with their corresponding electronic color set, once standard RGB values for each print have been determined. This can be done by monitoring the colors in each printing or print run as stated previously.

Additionally, the color sets would preferably include identifiers such as, but not limited to focus charts. The focus charts would preferably include concentric shapes or similar elements that would allow the System Software to detect multiple levels of focus accuracy by determining how many level inside the concentric circle it could detect fidelity and detail. The innermost portion of the focus chart being the smallest and therefore most apt to degrade. See FIG. 3

Similarly, a QR code or similar element could be employed. For instance, if the System Software could read the QR code, than this determined that a threshold of focus was present in that part of the picture. Similarly other means of focus grading would help determine if the focus fidelity of the image was acceptable, thus saving time by rejecting poor, unacceptable image quality and erroneous or poor medical records that do not serve their intended purpose of representing the patient or subject.

This is a fundamental advantage to this System—it provide many novel, non-obvious and useful means to produce standardized, controlled, consistent, improved, audit able and track-able pictures and related data in medical related fields.

For This Section—See FIG. 4 as well as FIGS. 1a-d & 2

As described above, the picture is taken and image is displayed preferably electronically.

Preferably, the matching electronic color set would then be attached to the picture, so that the viewer can see both the physical color set in the picture and the electronic one below it. Alternatively, the electronic color set can be displayed with the appropriate.

Preferably the System Software device adds the matching electronic color set to the picture, preferably outside the picture, so no content within the picture is obscured. It is attached in an adjacent position/orientation, so that the viewer can see the printed color set alongside the matching electronic color set. This can be attached to the picture permanently as a single image or file, or by saving the data with the image in a single file, as separate layers. Alternately, the information can be saved so that the electronic color set can be displayed together with a picture with a corresponding printed picture set at a future point in time. It also may be that the electronic color set can be made either visible or invisible. Preferably, once attached, the image is locked, and immediately identifiable as a product of the System Software.

One important purpose of presenting the electronic and photographed version of the color set simultaneously, is to present the viewer a means of subjectively evaluating the correspondence between the two color sets based on objective, scientific and verifiable standards. The two sets should match if the conditions, photographic process and/or display have not adversely affected the printed color set in the photo. This method of presenting these two devices for this purpose of evaluation is extremely useful and is one of the claims and purposes of this invention. It provides a means of judging the color set's fidelity, and therefore, of all the content of the picture.

The invention is comprised of the individual devices and methods, as well as the collective means and devices that achieve this.

There are many variations on that can produce this result, which we believe have or will be described in this document. However, preferably having a mass produced color set presented with a matched electronic version of the same color set that can account for anomalies of mass production and the inevitable variations of people or behavior, capture devices and conditions or technical variables to produce a means of comparing these two sets that provides the viewer with a means to judge the correctness and correlation between the two standards: the color set in the picture and the "electronic" version that is the same color values expressed or translated into the color space of the desired display is preferably a central practice in this invention.

Additionally, the system software may display an/or embed visible and invisible watermarks, including digital watermarks in the image itself. This can be accomplished with Digimarc®, or some similar, third party provider. Preferably, the watermarks would be employed to designate the pictures as calibrated and/or processed, as well as to track the image and/or any alteration to it and/or prevent or deter such alterations, thus providing a means of tracking and maintaining the integrity of the picture. Additionally, this step would protect the provenance of the image so that it can best represent its subject particularly in the field of medicine or related fields over time as this integrity is valued as part of the medical record.

Visually comparing the corresponding electronic and printed color sets provides a means for the viewer to see and analyze the correspondence of the color set in the picture with the matching electronic version of the color set. This visual comparison gives the viewer the ability to judge the quality of the color set in the picture, and therefore, the other contents of the picture.

Likewise, comparing the RGB numeric values of the each color in the printed and electronic color sets is another form of verifying and analyzing correspondence of the colors in each set. See Color Calibrating and Color Certification below.

Alternatively, the Calibration Slate or similar device could be utilized as part of a System or separately as a guide or norm in the picture without the electronic color set as reference.

Alternatively, the printing of the color set or Calibration Slate could conceivable be printed with an acceptable deviation from the standard such that tracking each print run is not deemed necessary.

Alternatively, the color set or Calibration Slate can be printed as an adhesive label to adhere directly to the subject.

Alternatively, the color set or Calibration Slate can be printed without cm or ruler markings on it.

Alternatively, the Calibration Slate can be printed as a label or sticker, which could be attached to an existing object such as a wound ruler or similar device. Similarly, the label version of the Slate could be adhered directly to the subject. Thus additionally the Slate could be used to calculate the curve of the object to which it is attached by having the System Software read elements on it to identify and calculate curvature. Examples of such elements are known geometric shapes such as squares, QR codes, bar codes to name a few. These techniques also apply to the Wound Label, see that section as well for more information.

This device and method remains the same with "moving" pictures as well. Such moving pictures may include but are not limited to forms of video, animation, and motion picture photography.

Part 2: Means of Color Calibrating Images:
After performing the above.

The System Software identifies the color squares in the color set, reads the RGB value of each color, matches the printed color set to a print run, and retrieves the standard RGB values for that run. Device calculates "Calibration Factor" (where the Calibration Factor is the amount the red, green, and blue components within the RGB color space vary from the target values for each color, which therefore indicates how much adjustment is needed for each color in order to bring it back to the standard).

When using a software to read and determine the color space of a color such as "color picker" tool in PHOTOSHOP, it is important to define the size of the sample size it is reading or "picking." It is preferable that the size be greater than one pixel as any single pixel may not be indicative of a color sample. It is also preferable that it not be excessive so that it average too many pixel and is therefore not as precise in its reading. Tests have indicated that around 4×4 pixels is preferable.

Device applies the Calibration Factor, based on unique identifiers for the printing (or each individual) color set in the picture so that their RGB values match the corresponding, known RGB values. This will now match their values to what the values were prior to variables being introduced by the various equipment, the environment, and the picture taking process.

Ways to Calculate the Calibration Factor:
Identify the RGB values of a grey square. Compare identified values to target values. Use RGB delta of grey from the target to calculate the Calibration Factor. See FIGS. 7a-c which show the Calibration Factor and it's source, i.e. the difference of the picture values in RGB from the target before calibration. In this case the calibration factor is the mathematical figured by which the R, G, and B are multiplied to bring their value back to the value of the target.

Alternately, identify the RGB values of one or more color squares, and calculate the difference from the norm.

This device and method remains the same with "moving" pictures as well. Such moving pictures may include but are not limited to forms of video, animation, and motion picture photography.

Part 3: Means of Color Certification of Images:
See FIGS. 1a-d, 2, 4, 6, 6a, 7a-c There are several aspects of Certification. Preferably the System Software would perform a variation on each of these. Alternatively, the System Software may perform one or more of them in any combination. Alternatively, the System Software may perform the following:

1) Certification of the Print Run. The identifier on the color set would be read by the System Software so that the corresponding target values and electronic color set can be retrieved and utilized for Calibration. Preferably a unique QR code or similar element on each slate is read by the software (or typed in manually.)
2) Preferably the System Software Verifies that the indentifying number (a) is not an unauthorized copy, (b) has not been used by on a different patient, facility, date, user or any other use that may be deemed non-conformant to the field's "Standard of Care" or Best Practices.
3) Preferable the System Software records information regarding the user, camera, subject, date, time, facility or similar information obtained either from a third party EMR or by some verifiable means, and stores this in a way that tracks the information, and/or attaches it to each picture. Thus establishing and tracking the provenance of the information and the corresponding picture.
4) System Software preferably verifies that the picture has not been altered, degraded, otherwise compromised or "PHOTOSHOPED."
5) System Software locks the picture visibly and invisibly in order to deter, track and/or detect alterations to the picture.

Preferably all colors in the color set or Calibration Slate would pass for the picture to be Certified.

Alternately, any number of colors which pass could be used to determine whether or not the image is certifiable, with or without any of the other elements.

The electronic version of the color matrix will preferably have the colors filled in based on the readings from each printed batch of charts. It will match the chart, rather than the printed chart trying to match it. After reading and calibrating the color chips, the device certifies that the colors are within an acceptable numeric variation from the known target values.

The acceptable variation is based on an "Increment of Discernible Difference," discussed in Part 3a, below.

To establish that the User's display is of acceptable quality:

It is recommended that the user calibrate his/her monitor using common means, such as the X-rite i1, Colormunki, manufacturer's instructions, etc.

Alternately, the viewer can hold a printed color set and compare it to a large electronic version of the color set displayed on the screen to determine whether or not he/she sees the colors as a match.

If the color sets don't appear to match, then, it is highly recommended that the viewer calibrate his/her monitor.

This device and method remains the same with "moving" pictures as well. Such moving pictures may include but are not limited to forms of video, animation, and motion picture photography.

Part 3a: Method and Device (the Device being the Formula) to Define an Increment of Discernible Difference in Display of Colors by Use of "Color Formulas."

As described in FIGS. 9a-i, each color has a unique and proprietary formula for calculating whether the RGB values fall within an acceptable range. The acceptable range means that it falls within a range that should not be typically discernible to users. This is referred to as the "Increment of Discernible Difference."

One process for obtaining our increments of discernible difference is through testing multiple viewers (clinicians) to determine the minimum variation of color that is discernible. There are many means to test viewers to determine a statistically meaningful increment of discernable difference. Alternately, this can be accomplished by showing a standard color in the set alongside multiple variations of that color, and then asking viewers to choose which ones match the standard color.

This testing can establishes an Increment of Discernible Difference for each color. Reading the RGB values of the variations and the standard determines an initial numeric value for the Increment of Discernible Difference. As colors are not made up of their RGB components equally, the range of variation of R, G and B is different for each color.

Preferably, one would calculate a numeric equivalent in the color space that corresponds to the Increment of Discernible Difference, i.e.—how far numerically from the target value of the correct color before the color shift is discernible. There are several ways to generate values pertaining to an Increment of Discernible Difference is to give a qualitative color test to clinicians, and ask them to tell you when the colors appear to change. You can then use the RGB values of the colors at the first IDD as bookends. Using a graphic program such as PHOTOSHOP, you can then find all combinations in the color space which will give you matching colors. The range of accuracy is different for each color. For example, green may appear the same at differences of 10 Red, 20 Green, and 30 Blue. Each color carries its own weight, which differs for each. Red, in the RGB space, carries a lot of value when creating the color green. Slight changes in the red value will affect the reproduction far more than a slight change in the blue color value. Thus the numeric margin of error can be calculated for each color.

Preferably, a proprietary formula for calculating the numeric combinations of R, G and B for each color can be devised. The formula for each color describes the possible numeric range of R, G and B values that will render a color that is NOT seen as discernibly different from the standard color. The System Software uses these unique formulae for each color to determine whether or not it is certifiable.

The formulas and graphs in FIGS. 9a-i describe the ellipsoidal area that is within the Increment of Discernible Difference for each color. The formulas that have check marks next to them (the other formula is not "turned on" and describes the RGB values as a plane, for reference) describe the axis and ellipsoidal range of the mathematical combinations of the R, G and B values that will produce a color that is within the Increment of Discernible Difference. FIGS. 9a-i represent the formula and graphs for each color currently used in the Calibration Slate or color set.

The method takes the RGB values of a color in the photographed color set and calculates the delta or difference of those values from the target RGB for each color in the set. In the three dimensional Graph, R, G, and B are the three axes and where they intersect represents zero difference from the target value. Therefore, each color can be plotted in the three-dimension graph by its three coordinates. The coordinates are the difference of the color from the target.

Therefore, each color can be plotted in the graph and its position is either within ellipsoidal area that is not discernible or not. Therefore each color tested with the formula is given a pass or fail.

Similarly, the sum distance from the foci and other relevant data calculated to provide more specific positioning of the colors in the color set for each picture for more precise means of mapping whether the colors are acceptable or not. See FIGS. 9a-i.

Therefore, the formula is the device to mathematically ascertain if the RGB value of any color is within the Increment of Discernible Difference and is therefore acceptable.

Alternately, the parameters of the formula can be adjusted to allow less or more deviance from the target values of the colors in the color set. Alternatively, another mathematical means of defining a similar acceptable range for the values of each color in the color set (i.e., using a statistical calculation to define an "margin of error" that is acceptable.) can be employed for similar purpose. Alternatively, other means of establishing an Increment of Discernible Difference can be employed such as but not limited to testing wider set of users, different approaches to the testing of colors such as asking the participant to adjust a color until it matches or they are able to differentiate if from the target. Alternately, a statistical method of analyzing information on human sight or similar research could produce a margin of error, which is defined an Increment of Discernible Difference.

The Number of Colors that Passed or Failed is Represented and Recorded in the "Matrix" or "System Software Matrix." See FIGS. 7a-c for Sample Matrix The System Software Matrix is the chart for each picture that quantifies the information for that picture. Preferably, the Matrix documents all information regarding the picture. This information includes but is not limited to: information regarding the print run, identifier(s) on the printed color set, target or known values of the print and matching electronic color set, information regarding the user, camera, subject, date, time, facility or similar information, information regarding the values of the colors before and after calibration, the Calibration Factor(s), the delta or difference in RGB values of each color from the corresponding standard or target before and after calibration (or similar method of expressing color numerically), the results of Color Formula processing (i.e. graph, "pass/fail" status and sum distance from foci), measurement anchor positions and/or coordinates, measurements generated by anchors (i.e. length and width of subject or wound) and any information generated by the System Software regarding the picture or the picture's environment or category.

The Matrix is generated with each image and stored in the System Software preferably in a way that tracks this information with each corresponding picture and/or store it in the image (such as but not limited to metadata). Other associated information will preferably be part of the Matrix. The Matrix provides statistical analysis of images and groups of images, and remains tied to the image in the future for reference.

Part 4: Method and Device for Consistent Image Photography in Medical Related Photography.

See FIGS. 10 and 11, 12

The system may include a Framing Assistance Guide that appears on the viewing portion of the image capture device, and assists the user in alignment and orientation of the image for improved quality, consistency, and optimized reading of the image by System Software. The guide is visible on the display as an overlay, such as etched, applied as a decal, or electronically generated, with the subject and color set appearing behind it. (see examples below). Specific devices can be recommended, and specific pre-determined settings used, so there is an additional reduction of variation and external correction.

The Framing Assistance Guide is preferably visible during the process of setting up and capturing the image, whether still image or live video etc. (herein referred to as simply "image" or "the image" for ease of discussion).

Thus the Framing Assistance Guide is both a device on its own with beneficial uses and as an integral part of the System with its System Software.

The purpose of the Framing Assistance Guide is to give users a clear means of consistently framing and orienting their images. The fixed relationship between the subjective part(s) of the image (center of the wound or subject) with the constant (the slate) provides consistency in framing for a variety of subjects and subject sizes.

There are two or more fixed elements on the viewing portion of the picture-taking device. The fixed elements are used by the operator to align elements of the subject prior to taking the picture. This will provide consistent framing relative to the subject and these elements, regardless of distance from the subject, picture-taking device or the focal length of its lens, etc.

Furthermore, the alignment of the slate with the line in the Framing Assistance Guide provides a simple but critical means for the user to keep the camera perpendicular to the subject. This effectively creates a means of aligning the capture device or camera to the slate and subject in three dimensions (using the x, y and z axis). Please note the preferred slate placement is on the skin on or near the subject (such as just outside the periwound area). The slate may be adhered to the skin as per the adhesive section on the back of the wound slate. This will keep it on the same plane as the wound.

This can be enhanced greatly, but is not dependent on a System Software system that interacts with the capture device, the subject and the user (see below). The Framing Assistance Guide currently contains, but is not limited to the following features: crosshairs for centering wound, line for aligning slate/color set, and head and foot indicators for orientation.

Furthermore, elements on the framing assistance guide can refer to elements of the subject or its environment outside the visible frame of the picture. Examples of these elements are the icons of the head and foot, referring to where the patient's head and feet should lie outside the visible frame. Following these guides provides a means of taking pictures that are oriented in an anatomically consistent and correct manner. See FIG. 8, for example.

This device and method remains the same with "moving" pictures as well. Such moving pictures may include but are not limited to forms of video, animation, and motion picture photography.

Part 5: Method and Device for Taking Displaying, Realigning, and Auditing Planary Measurements in Photographs and Tracking Subject Measurement Using Pictures.

See FIGS. 13a-c

A picture is taken with an object that has a known sizes delineated on it, preferably an object or element that can be read by a System Software such as a QR code, or similar device, which contains information that can be passed along to the computer software. Included elements may contain, but are not limited to, batch number, facility name, color information, certification date, etc. See Matrix description above.

The System Software identifies and reads the object. It calculates the pixels size of the object to then derive scale size of the object in that particular picture (i.e.—pixel to millimeters).

The System Software then displays anchor points for the user to position at the edges of the subject such as lesion to indicate the points between which the System Software should measure the distance. The pixels between the points are converted to increments such as millimeters. The distances such as length and width can then be exported to other software.

The anchor positions of the anchors are also calculated such as using the pixel's x & y positions of in the image. These positions or coordinates are then stored.

The visual anchor can then be removed from the image without losing its position and thus the reference points for the measurements.

The System Software provides a means of removing the images visually and later re-displaying them accurately. Alternatively, the anchors are on layers or other means of turning them "off and on."

The System Software may allow the same or different user to reposition the anchor points and generate new measurements that can be exported. The device stores and tracks all the position and preferably the user, time, date etc. to track these changes.

As an example of an intended application, currently clinicians are often paid by the size of the wounds that they treat. But typically there are no means to see where the measurements were taken from, only the recorded length and width or similar measurements, but no means to derive from what point to what point was measured. The System Software provide a means to see where the anchors were place that generated those measurements so that they can be verified, audited and even corrected. Thus this System allows for meaningful oversight where there is currently none.

See FIGS. 4-6

The System Software has a means of identifying the picture on which it is displaying these anchors such as a file name, type etc. The device may also store other data such as picture size, date, user ID, subject ID and related information.

The System Software stores the anchor position coordinates and the indentifying image information plus other relevant data, also referred to here as "data." Data may be stored in a database with our without the image for the purposes of displaying them together. Similarly, the data could be stored in the in the image, such as but not limited to the metadata of that image. Similarly, the data could be remain displayed on the image, and/or with a means to make it visible or not visible. Similarly, the data can be stored and retrieved with the image in any means that allows the data to be retrieved and used to indicate the anchor positions on the corresponding picture.

The System Software can then track and reproduce the position of anchors in multiple images over time, and also track the time/date and other indentifying information regarding the viewer, the picture, the subject and the anchors.

In this way, the device provides a method to track and audit the anchor positions, corresponding measurements and related information such as the user, time, date etc. as well monitoring/protecting the integrity of the picture information and the marker positions.

Part 6: Method and Device for Attaching a Calibration Slate or Similar Device to a Patient or Subject.

The "Angle Device" is a small, angled object such as a 1"×2" piece of card stock with adhesive on one or both of the outer sides of the angle. The adhesive sticks to the patient or subject on one side and the Calibration Slate or similar device on the other. Note: The Calibration Slate has adhesive on the back, so the angle device may only need adhesive on one outer side of the angle to perform.

The angle device provides a method of adhering the Slate or similar device to the patient or subject when there is no skin or surface in the area of the wound or subject being photographed on which to mount the Slate or similar device.

For example, when photographing a heel, toe, or amputated limb, the lesion or wound may not have any surface around it that is on the same plane as the lesion or wound, therefore an angle device is used to attach the color set or calibration slate.

See FIGS. 3a-c.

In these cases, it becomes necessary to give an alternate option for mounting the Slate on the same plane as the wound or lesion (etc). This mount is accomplished by attaching one outer side of the angle to the body part, i.e. "under the lesion or wound, and the affix the Slate or similar device to the other side of angle.

See FIGS. 13a-c.

This device provides a method for the Slate to be mounted on the same plane as the wound or lesion, so both can be photographed without holding the Slate. Furthermore, these provide a means for more accurate planary measurements, when derived from the photograph.

Part 7: Method and Device for Calculating and Cataloguing the Relative Distance, Skew, and Anatomical Orientation of a Wound in a Photograph.

Background: It is common practice in wound photo documentation for the clinician to place a simple white label near the wound with the corresponding number of that wound in the EMR. Typically this label is white paper with an adhesive (such as those produced by Avery Inc), ranging in size from 3/8"×5/8" for smaller wounds, to 1"×2" for larger wounds. This device improves upon this in ways that are new, useful and non-obvious.

The "Wound Label Device" uses a similar label preferably with adhesive on one side placed near the wound or subject with the correct wound number for the photographic documentation.

The Wound Label Device preferably has element(s) printed on it, such as arrows, a QR code, a color square, or something similar, that allow the System Software, or similar software, to identify and read that object. The System Software calculates the number of pixels of the object in the picture and has the actual size of the object in its memory. The System Software uses the known size of objects such as the QR code or square to determine the pixels per cm for that photograph.

Using this information, the System Software can then determine the distance between the corners of the QR, color set, and/or the length of each side of the square, to calculate the skew in the picture.

When used in combination with the Calibration Slate or similar device, the Wound Label Device provides a third data point regarding the position of subject in the picture.

This provides a method to triangulate the position of the wound or subject, creating a more accurate means of (1) calculating the planary measurement of the wound using anchor positions (2) determining the skew of the picture (3) mathematical means of calculating whether or not the plane of the Calibration Slate is the same as that of the wound or subject.

Alternately, boxes placed equidistantly among the slate can be used in the correction of Key stoning. This may include any shape identifiable by a computer system. The distance between them is known, and any difference indicates that the calibration chart is curved. This may also include shapes placed at each corner, and in various, equidistant places throughout the chart.

Current medical protocol indicates that the head of the patient should be "above" the top of the frame. Similarly, the bottom of the frame should "point to" or be oriented toward the feet of the patient.

The Wound Label Device preferably includes means of indicating the correct anatomical orientation for the subject in the frame such as an icon of the head with an arrow pointing up.

The System Software can read the objects and information on the Wound Label Device such as a QR code and automatically orient the photograph so that the top of the photograph is pointed toward the patient's head. Alternately, the physician can choose an orientation of their liking, and the software can rotate it to the preset preference.

The Wound Label Device(s) in combination with a System Software is therefore a method and means of:
(1) numbering the wound in a means readable to a software
(2) indicating orientation in a means readable to a software
(3) providing a means of having the software automatically orient the picture (assuming the user has placed the Wound Label Device properly)
(4) calculating scale in the picture by a software
(5) calculating relative distance from the other elements such as a Calibration Slate, additional Wound Label Device or other elements (by a software) in the picture
(6) using known sizes and positions of the elements on the Would Label (such as but not limited to QR code or boxes) to calculate skew base on how far off the different sides/parts of the element are from their known proportions and sizes,
(7) using the known value of the elements compared to how these elements are represented in the photograph to identify, analyze and/or calculate the curvature of the subject that the Wound Label is adhered to
(8) providing a means to triangulate or otherwise mathematically map the differences such as but not limited scale, skew between the relative position of the Wound Label and other data points provided in the picture such as but not limited the color set or calibration slate (9) identifying the plane of the wound relative to plane defined by the Calibration Slate or similar device

(10) indentifying, analyzing and/or calculating the difference in the plane of the subject versus that of the Calibration Slate (if any)

(11) calculating the accuracy of planary measurements based on how accurately the plane of the Calibration Slate is representing the plane of the actual wound or subject and/or

(12) indentifying, analyzing and/or calculating the curvature of the actual wound or subject All of the methods above can be used separately or in any combination.

In this entire document, for brevity, when the terms such as the Calibration Slate, Angle Device, and Wound Label Device are used, it is short hand for those objects/devices as well as a similar device.

Part 8: Method and Device for Creating Measurements, Consistency, Tracking and Audit Ability in Medical Related Photography with a System Software.

The System Software described in this document may be implemented in any computing device or system that runs software. Examples include but are not limited to a stand-alone software on a local device such as laptop, desktop computer or mobile device such as an iPhone, iPad, tablet or other smart phone or table or device yet to be invented.

Similarly, the System Software can run on a network, "cloud" or other nonsite specific host, or a combination of both such as on a mobile smart phone uploading images to a cloud based server system. See FIG. 18, for example.

Similarly, the System Software can run by itself or in conjunction with another software such as but not limited to Electronic Medical Record software or software providing telemedicine and/or telehealth services.

In general, the System Software allows for any or all of the core features of color reading, calibration, certification, measurement, anchor points for measurement.

The following list represents additional preferred functions of the System Software. The System Software may include, but is not limited to:

The System Software will preferably use anchor points to electronically measure the area of a wound (FIGS. 19a-d). The user can drag the anchor points to spots representing the edges of width and height, and the System Software will enter the measurements and calculate area. The System Software can utilize the known size of the aspects of the Calibration Slate or similar device to map the correspondence between the pixels of the image and the "real" distance of these aspects to then correctly extrapolate the "real" distance of any part of the image.

The System Software and the system are preferably designed to accommodate the inconsistencies of each print run. All due effort will be made to maintain the same exact color values for each print run however the variance of each run will preferably be measured and then used to form the new, actual standard for that print run. Each print run will preferably have a separate identifying number, a "batch number" so that the printed versions of the slates in that run can be calibrated to the standard for that run. Thus, each print run will preferably be measured, tracked and calibrated as a closed numeric set so that they are correct within each run and known, quantified correctness to the all other print runs.

For visual verification of each print run, there will preferably be an electronic version of the slate made for each print run that is correct to actual standard for that print run again so any slate from that print run can be compared to the correct standard of that print run.

The System Software will preferably populate the colors in the electronic version of the matching color set with the correct color values for the corresponding colors for that print run. Therefore, the variance of any colors in the set are represented by the corresponding electronic calibration slate in the photo. This is used primarily for qualitative analysis.

The System Software preferably displays the actual values obtained by processing the image, and displays a degree of variation in a color values report.

The System Software will preferably correct images using the target values obtained at press. These values represent the target values for the System Software's color space, and are based on the final printed pieces.

Deployment of System Software
See FIG. 15

We have described three models of Deployment of the System Software (SS) system below. There are basically 2 parts to the SS system, the SS Engine and the SS Database (DB). The SS Engine is a stand-alone system by itself and does not necessarily require a DB component. However, without a DB component, the data generated during the Analysis of the uploaded images and the data generated during the Calibration will only be stored as Metadata within the image itself. This makes the data very hard to get to and to search for or identify a particular image, all the image files stored on the server would require to be read and processed, which would be a time consuming and tedious process. Instead, if all the data generated by the SS engine is stored as a DB, then it becomes easy to search and extract information about any image.

The models described below therefore assumes that there will be 2 components, namely the SS Engine and the SS DB that will constitute the SS System.

The SS Engine can be deployed as a Plug-in, where it would become part of a Web Application (developed using .NET in Windows) and would be integrated with the Web Application. Another option is to deploy the SS Engine as a Stand-alone Web Application with a well-defined interface such that other Web Applications (Like the EMR's web app) could interact, send and receive data from the SS system.

The SS DB is designed to be sufficiently independent in terms of deployment from the SS Engine that it can be installed either on the same machine (server) as the engine or on a separate machine so long as there is a consistent network connection between the two machines.

Also the distinction between the SS DB and the EMR's DB should be made here. The EMR's DB stores data relating to the EMR's application which enables it to display the patient records and other information relating to its functionality. The SS DB relates to information generated by the SS System (including the SS Color Matrix etc.).

The Three Models for Deployment
1) Embedded Model
2) Saas (Software as a Service) Model
3) Data Protection Model.

First, a description of the Servers that may be deployed to implement the system. The Server described as "The EMR's Server" would be owned and managed the EMR into whose system we intend to integrated the SS system. This means that all software, components and data stored in the EMR Server would be managed, serviced and backed up by the EMR and SS would only have limited access (if any) to the software and data stored in the EMR's server. The Server described as "The SS Server" similarly would be completely owned and managed by SS and therefore anybody else would not have any access to the software and data (including the DB) without the explicit permission of SS.

Embedded Model: In this model, all the SS Software and the SS DB would be housed in the EMR's Server. Once we assist in the integration and configuration of the SS Engine, the EMR would have complete control over the engine and the data. Therefore if there is any Proprietary or Confidential data, this would also be stored on the EMR's server and the EMR would have complete control over it.

However, in this model the image data would have to move only from the Client (User's Browser) to the EMR server and back (after processing) from the EMR Server to the Client machine (2 Hops). Thus the delay caused by moving large amounts of data ("The Image" data) across the Internet would be minimal in this model.

Saas Model: In this model, the SS System is completely separated from the EMR's application with only a well-defined interface provided by the SS System that will enable the EMR's application to send Raw Image data and get back Processed Images from the SS System. In terms of data security, auditing etc. this is the best model as SS will have complete control over the Images being processed and the data accrued out of it.

However in this model the Image Data would require to move first from the Client (Browser) to the EMR's Server, then from the EMR server to the SS Server for processing and then back from the SS Server to the EMR server and from there to the Client machine (4 Hops). Therefore the delay caused by moving large (3-4 MB) blocks of data over the internet may be a serious issue in this model.

Data Protection Model: This model takes the best of both the models described above and tries to build an efficient system. In this model, SS would be implemented as a Plug-in and therefore housed within the EMR's Web Application. However, the SS DB would be housed in a separate server owned by SS. Therefore all the data accumulated by the SS system would be under the control of SS. Note that the amount of data relating to the processing of an image would be in the range of 1-2 Kilobytes and would take negligible time to move from the EMR's server to the SS Server, it is the Image data (in the range of 3-4 MB) that would cause serious delays in transmission over the Internet. In this Model, the image is processed on the EMR's server and therefore it would only require 2 Hops (from the Client to the EMR's Server and back from the EMR's server to the client) during processing. At the same time all the Proprietary or Confidential data is stored in the SS Server owned and managed by SS.

The only issue over here is how to handle situations when the Internet connection between the EMR server and the SS Server is lost for any reason during the processing. We have two options: one is to allow the image to be processed and thereby lose the data related to that particular image's processing, and the other is to prevent images from being processed if the connection between the servers is lost.

The System Software Interface

See FIG. 16

This section will describe the interface (interaction) between the EMR's application and the SS System. Here, the distinction between deploying SS as a Plug-in or as a stand-alone application (SaaS model) will not be made as the Interface conceptually would be similar even though technologically, the interface between an application and a plug-in and between two web applications may be different. In the context of this discussion we will describe the Interface generically to include both these scenarios.

In the context of this discussion, the EMR's application will always be the driver as the Users will always be interacting with the EMR's application first. The SS system will get control only when the EMR's application notifies the SS System of the fact that an Image has been uploaded and would require processing. The uploading and storage of the Raw image would be the responsibility of the EMR's application and would not be different from what they implement presently to accept and store wound images.

Once the EMR's application uploads and stores the wound image in their server, EMR should 'Invoke' the SS interface which can then process the image. At the end of the processing, the SS system will have a 'Processed' image, which should be handed back to the EMR's application to complete the transaction. Another transaction implemented by the SS system is the Wound Measurement sub-system. This transaction can only be invoked after the SS System has successfully processed an image. The SS system must have a successfully processed image on which the Wound Measurement sub-system can work on. Therefore after the first transaction successfully processes an image and hands it over to the EMR's application, the Wound Measurement transaction can be 'Invoked' to allow users to define the Anchor positions on the Wound, identify the length, width of the wound and calculate the area of the wound. The calculations are all part of the SS System and at the end of this transaction, the SS system can hand over to the EMR's application the Wound Measurements to store in their DB to complete the transaction.

The System Software Interfaces

See FIG. 17

As mentioned above, the EMR application always drives the processes and 'Invokes' the SS system to perform services for it. FIG. 17 describes the two Major interfaces that the EMR application can use to perform actions in the SS System. The First interface "Process Image" is invoked after the user has successfully uploaded a wound image and the EMR application wants that image to be Processed. When this interface is invoked, the Full Path of the Raw image to be processed, the Identity (Name, Key etc.) of the Patient and wound in the EMR DB (to maintain the DB Relationships) are passed as parameters to the SS System. The SS System after processing the Image will return the Status (Success or failure, the Processed image, Color matrix, Unique serial number etc. back to the EMR Application.

As the figure above indicates, the Wound Measurement interface is independent of the Process Image interface and it can optionally be called by the EMR Application for Wound Measurement. The only condition for Wound Measurement is that a successfully processed image must be available for the SS system to successfully measure wounds. Similarly if the EMR application does know the Initial anchor positions (or if the Patient/Wound identity is passed, then SS can extract the Anchor positions from its own DB) then they too can be passed to the SS System. The SS System then prompts the user to place the Anchors to correctly identify the boundaries of the wound and measures the Wound area. This data is then returned to the EMR Application along with the final Anchor positions (if the EMR application is managing this data in its DB).

A preferred embodiment of the System Software as a plug-in within an EMR servicing wound care photo documentation.

Below constitutes the functional specifications for such an embodiment, describing the User's activity, the basic interaction between the System Software and the EMR or similar device.

A. Functional Specification (See User Interface Figure)
PRE-TS Plug-in—User selects specific patient and wound in EMR OR SIMILAR SOFTWARE 1. Image Selection:
   User in EMR OR SIMILAR SOFTWARE clicks "Upload Picture" in EMR OR SIMILAR SOFTWARE
   EMR OR SIMILAR SOFTWARE Browser opens a browser window for image selection
   User selects image to upload
   (Image selected will hereafter be referred to as the "Current Image")
   TS Plug-in Opens—
2a. Display: Display: "Anticipation" Window shown to User as Step 2b is processing.
   (TS designs content of Window)
2b. Processing Current Image (not seen by User)
   EMR OR SIMILAR SOFTWARE delivers to System Software Plug-in: Current Image, Facility ID, User ID, Patient ID, Wound #, as well as IP address, OS, and Browser used by the user.
   System Software Plug-in processes and calibrates Current Image, and reads unique Calibration Slate Number (CS#)
   If System Software Plug-in cannot read CS#—refer to Popup A
   System Software Plug-in sends CS#, Facility ID, User ID, Patient ID, and Wound Number to System Software Server
   System Software Server synchronously* determines whether or not this Slate is used appropriately as defined by System Software: *(Asynchronously if System Software Server down)
      If YES—
         System Software Server verifies use of CS# to System Software Plug-in, allowing for System Software Certification
      If NO—
      System Software Server rejects use of CS# to System Software Plug-in, image is marked "Uncertifiable & Invalid Slate Number"—refer to Pop Up B
   System Software Server records Current Image process initiated (to be closed when "submitted" in EMR OR SIMILAR SOFTWARE)
   System Software Plug-in embeds Certificate on Current Image and marks them as either "Certified" or "Uncertifiable"
   System Software returns Current Image to EMR OR SIMILAR SOFTWARE
   EMR OR SIMILAR SOFTWARE delivers URL of processed Current Image to System Software Plug-in for display in browser
   EMR OR SIMILAR SOFTWARE delivers URL's of Thumbnail Images for two previous images of current wound to TS Plug-in, along with corresponding length, width, depth, anchor point coordinates, and date submitted into record.
3. System Software USER INTERFACE OPENS
   Section 1—System Software Logo
   Section 2—Current Image marked either Certified or Uncertifiable in the Certificate
   Section 3—Previous image thumbnails with anchors, dates, and measurements
   Section 4—Current Image measurements
   Section 5—EMR OR SIMILAR SOFTWARE buttons: Upload New Image, Cancel & Save
   Section 6—EMR OR SIMILAR SOFTWARE top window bar, displays wound number etc.
   "Cancel" will abort System Software Plug-in and send message to System Software Plug-in/Server accordingly
   System Software UI will be as large as possible, coordinating with EMR OR SIMILAR SOFTWARE. System Software may elect to have image zoom feature.
Exception 3a:
   IF the CS# cannot be read by System Software System Software: 50
      Display Popup A—User manually enters Slate # into System Software Plugin.
      System Software Server synchronously* determines if this Slate is used appropriately: *(Asynchronous if System Software Server down)
   If YES—
      EMR OR SIMILAR SOFTWARE returns Current Image to System Software Plug-in for reprocessing and embedding of Certificate.
      TS Plug-in returns Current Image to EMR OR SIMILAR SOFTWARE
      EMR OR SIMILAR SOFTWARE delivers URL of Current Image to System Software Plug-in for UI display in browser
      User continues with Step 4a or 4b accordingly
   If NO—
      System Software Server rejects use of CS# to System Software Plug-in, image is marked "Uncertifiable and Invalid Slate Number"
      Display Popup B—User chooses either:
         Choose new image (return to Step 1 WITHOUT leaving System Software UI) or
         Continue with "Uncertifiable & Invalid Slate Number" image
Exception 3b:
   IF the Color Matrix cannot be verified by System Software Plug-in:
      Display Popup C—User manually verifies Color Matrix position in System Software UI.
   If it CAN be verified—
      EMR OR SIMILAR SOFTWARE returns Current Image to System Software Plug-in for reprocessing and embedding of Certificate.
      TS Plug-in returns Current Image to EMR OR SIMILAR SOFTWARE
      EMR OR SIMILAR SOFTWARE delivers URL of Current Image to System Software Plug-in for UI display in browser
      User continues with Step 4a or 4b accordingly
   If CAN'T be verified—
      Current Image is marked "Uncertifiable" proceed with Step 4b
4a. IF Certified:
   Current Image displays anchors for measurement
   User reviews previous anchor points and places anchors on Current Image
   System Software Plug-in generates length & width from anchor placement
   User manually enters depth
   User selects Save (Section 5)
      System Software Plug-in delivers anchor coordinates, length, width & depth (manually entered depth) to EMR OR SIMILAR SOFTWARE.

EMR OR SIMILAR SOFTWARE delivers length, width, and depth to appropriate fields in patient record WE will deliver the measurements and anchor positions to the TS Plug-in at the server for verification and analysis IF measurements are approx. >20% off, Popup D will prompt User to either:
Choose new image (return to Step 1 WITHOUT leaving System Software UI)
OR Reposition anchors on Current Image
OR Accept measurements (TS will tag image accordingly)

4b. IF Uncertifiable:
Popup E prompts User to:
Choose new image (return to Step 1 WITHOUT leaving System Software UI)
Choose "override" option
Choosing "override" will either prompt Popup F, or return User to Step 4. Image will be marked "Overridden".
Popup F (If necessary) prompts User to either:
Choose new image (return to Step 1 WITHOUT leaving System Software UI)
Place Red Anchors and Save—Return to step 4

6. System Software USER INTERFACE CLOSES
NOT in System Software Plug-in:
User finishes wound documentation and chooses "Submit" to enter System Software Image and associated data into EMR OR SIMILAR SOFTWARE database.
EMR OR SIMILAR SOFTWARE sends confirmation of data into their database to System Software Plug-in
Asynchronously, System Software Plug-in sends info to System Software Server to "close"
Current Image process as detailed in the API & Prototype program.

A Preferred Embodiment of the Mobile Application of the System Software Mobile Device App:

All of the current features can be performed on a mobile device as either a standalone, or a cloud-based version of the system. The mobile application would use known elements in the slate to guide the user toward correct framing of, and distance from the subject of the picture. It utilizes tactile and/or audio/visual cues to ensure proper framing, and would preferably take the picture automatically once a certain set of criteria were met. Those criteria, including but not limited to, may involve reading the QR code, color matrix, and skew detection arrows. It would measure the distance between multiple points in the arrows, ensuring that the slate is perpendicular to the device. If available, the mobile application would preferably change the color temperature of the flash, and diffuse it for even, consistent lighting.

See FIG. 20

The app would gather information from the phone, including but not limited to, the distance from the device to the subject, and the GPS location of the device, verifying its location. It would save this information to the record.

1. Web Application (System Software Cloud)
To allow end users to review, retrieve and manage photography submitted via the System Software mobile applications.
2. API (RESTful)
To allow remote systems (Mobile Devices, Third Party EHR Vendors, etc.) to submit photography for System Software Certification and/or additional processing.
3. Mobile Application (iOS and Android)
To allow end users to take photographs and submit them to the System Software Cloud.

Technology

Microsoft's .NET Framework will be the utilized for the Web Application and RESTful API. The primary development language will be C# for core server side functionality and JavaScript will be the primary development language for the front-end application (IE9+, Chrome, Firefox 3.6+ and Safari 5+). The iOS mobile application will be written natively in objective-C (iOS 6+ Required) and the Android application will be written natively in Java (Android 4.0+ Required).

The following frameworks will preferably be utilized within the project: jQuery, EntityFramework, WebAPI & MVC 4. Additional third party frameworks may be utilized at our discretion.

The application will preferably be hosted within the Microsoft Azure public cloud. The Web Application and API will preferably be developed as independent Web Worker Roles to allow independent elasticity as end user utilization increases. Microsoft SQL Azure will preferably be utilized for the storage of relational data, e.g. users, groups, images (ancillary information only). Microsoft BLOB storage will preferably be utilized for the storage of the encrypted photographic data.

Core Functionality
Role Based Security
Administrator—Employees/Members
Users—Anyone requiring the ability to submit photographs to the System Software cloud.
User Management
Web Application
Administrator
Add Users
Edit Users
Delete Users
Disable Users
Group Management
Web Application
Administrator
Add Group (Administrator)
Edit Group (Administrator)
Delete Group (Administrator)
Disable Group (Administrator)
Data Encryption
In Transit
A standard SSL Certificate will be utilized to secure any public facing end points.
The client will be responsible for obtaining the SSL certificate.
At Rest
All photographic data will be stored in encrypted form using the industry standard AES encryption algorithm.
Authentication
All users will require a username (email address) and password (preferably minimum 8 characters, maximum 8 characters, alphanumeric and symbols).
Web Application
A browser cookie will preferably be saved on the end users computer/device upon successful authentication. The cookie preferably will not persist between browser sessions, the end user will be required to log in with each use of the System Software cloud.
API The API will expose an endpoint for user authentication, e.g. https://www.System Software.com/api/1/authenticate. The endpoint will accept a username (email) and password, validate the credentials, create a unique session identifier (session length TBD) and then return the unique session identifier to the consumer. Subsequent calls to the API will require that the unique session identifier be passed to the API within an HTTP Header.

Mobile Device
  iOS—User credentials will be entered into a login view and the user will be authenticated via the API. The API will return a unique session identifier that can be optionally stored in the iOS keychain.
  Android—User credentials will be entered into a login activity and the user will be authenticated via the API. The API will return a unique session identifier that can be optionally stored in the Android User Preference.

Photography Submission
Mobile Application
  End users will be able to capture a photograph using their mobile device.
  End users will have the ability to re-take or submit for processing via the API.
  If an image is certifiable the end user will be notified as such.
  If an image is not certifiable the results from the System Software engine will be presented to the end user.
  Regardless of the certifiability the end user will have the option to take a new photograph and repeat the process.
  A static PNG (transparency) will be overlaid on the camera to assist the end user in aligning the Calibration Slate or similar device within the frame. The PNG graphic will be provided by the client. Photography Certification
  Photographs submitted via the API will be processed by the System Software Engine and confirmed to be certifiable or not.
  Uncertifiable photographs submitted via the API will be stored and the response from the System Software Engine will be returned to the consumer via a JSON payload.
  The mobile applications will utilize the response returned by the API to inform the end user on what specifically (provided by the System Software Engine) could not be located within the submitted photograph.

Photography Management
Everyone
  View Photographs
    Certifiable
      The default view will show all certified images sorted by date (most recent first).
    Uncertifiable
      The user will have the ability to toggle (via tabs) between certifiable and uncertifiable photographs.
  Download Photographs
    The list of photographs, certifiable and uncertifiable, will include a link to download the actual photograph.
  Delete Photographs
    Users will have the ability to delete photographs that they've submitted.
  Users will only have access to view the images that they've submitted The scope of the invention should be determined by the appended claims and their legal equivalents, and not by the examples given.

The invention claimed is:

1. A method of calibrating an image related to the medical field, said method comprising the steps of:
  capturing an image on an image recording device, wherein the captured image includes a calibration slate appearing in the image, wherein the calibration slate has a machine-readable print run number that identifies a batch of printed calibration slates which includes the calibration slate appearing in the image, a separate machine-readable unique identifier in the form of a bar code that individually identifies the calibration slate appearing in the image, and a color chart comprising a set of colors,
  reading the unique identifier and validating the calibration slate based on the unique identifier, wherein the step of validating the calibration slate verifies that the calibration slate was not previously used, thereby preventing cross-contamination between patients,
  measuring a numeric color value from a color in the color chart of the calibration slate appearing in the captured image,
  reading the print run number,
  associating the print run number with the batch of printed calibration slates which includes the calibration slate appearing in the image, wherein each calibration slate in the batch is substantially similar, wherein the measured numeric color value has a corresponding known numeric color value associated with the batch of calibration slates,
  comparing the measured numeric color value to the corresponding known numeric color value,
  calculating a variance between the measured numeric color value and the corresponding known numeric color value,
  calculating a calibration factor based on the variance between the measured numeric color value and the corresponding known numeric color value,
  calibrating the captured image by adjusting the colors of the image by applying the calibration factor to numeric color values measured from the image, and
  discarding the calibration slate after a single use.

2. The method of claim 1, further comprising the steps of:
  consecutively capturing one or more additional images of a subject,
    wherein the subject is the same in each captured image, wherein each of the one or more additional images includes a unique calibration slate appearing in each of the one or more additional images, respectively,
  independently calibrating each of the one or more additional images, and
  comparing each of the one or more additional images to the preceding image to qualitatively determine how the subject has changed over time.

3. The method of claim 1, further comprising the steps of:
  measuring a plurality of corresponding numeric color values directly from a plurality of respective calibration slates within the batch of printed calibration slates, and
  calculating the variance between the plurality of numeric color values measured from the plurality of respective calibration slates to verify that all slates within the batch are substantially similar.

4. The method of claim 1, further comprising the step of displaying on a screen the captured image including the calibration slate appearing in the image and a second color chart comprising a set of colors having known numeric color values, wherein each color in the set on the second color chart is substantially similar to a corresponding color associated with the batch of calibration slates.

5. The method of claim 1, further comprising the step of attaching the calibration slate to a subject using an adhesive attached to the calibration slate before capturing the image that includes the calibration slate.

6. The method of claim 1, further comprising the step of associating the calibration slate appearing in the image with a patient based on patient identification information included on the calibration slate.

7. The method of claim 6, wherein the patient identification information is machine-readable, wherein the method further comprises the step of reading the patient identification information.

8. The method of claim 1, wherein the calibration slate appearing in the image further includes a focus chart comprising concentrically arranged shapes, wherein the focus chart is configured such that it can be used for grading the focus of the image, wherein the method further comprises the step of focusing the image using the focus chart before capturing the image.

9. The method of claim 1, further comprising the step of adding a security mark to the captured image, wherein the security mark is configured to indicate whether the image has been altered.

10. The method of claim 1, further comprising the steps of: adding a machine-readable unique number to the captured image for indicating that the image is certified, and certifying the image by reading the unique number.

11. A method of calibrating an image of a patient's wound, said method comprising the steps of:
    positioning a calibration slate in a location adjacent to a wound on a patient, wherein the calibration slate has a machine-readable print run number that identifies a batch of printed calibration slates which includes the calibration slate positioned in a location adjacent to the wound on the patient, a separate machine-readable unique identifier in the form of a bar code that individually identifies the calibration slate positioned in a location adjacent to the wound on the patient, and a color chart comprising a set of colors,
    capturing an image that includes the wound and the calibration slate using an image recording device,
    reading the unique identifier and validating the calibration slate based on the unique identifier, wherein the step of validating the calibration slate verifies that the calibration slate was not previously used, thereby preventing cross-contamination between patients,
    measuring a numeric color value from a color in the color chart of the calibration slate as the slate appears in the captured image,
    reading the print run number,
    associating the print run number with the batch of printed calibration slates which includes the calibration slate appearing in the image, wherein each calibration slate in the batch is substantially similar, wherein the measured numeric color value has a corresponding known numeric color value associated with the batch of calibration slates,
    comparing the measured numeric color value to the corresponding known numeric color value,
    calculating a variance between the measured numeric color value and the corresponding known numeric color value,
    calculating a calibration factor based on the variance between the measured numeric color value and the corresponding known numeric color value,
    calibrating the captured image by adjusting the colors of the image by applying the calibration factor to numeric color values measured from the image, and
    discarding the calibration slate after a single use.

12. The method of claim 11, further comprising the steps of:
    consecutively capturing one or more additional images of the same wound, wherein each of the one or more additional images includes a unique calibration slate appearing in each of the one or more additional images, respectively,
    independently calibrating each of the one or more additional images, and
    comparing each of the one or more additional images to the preceding image to qualitatively determine how the wound has changed over time.

13. The method of claim 11, further comprising the steps of:
    measuring a plurality of corresponding numeric color values directly from a plurality of respective calibration slates within the batch of printed calibration slates, and
    calculating the variance between the plurality of numeric color values measured from the plurality of respective calibration slates to verify that all slates within the batch are substantially similar.

14. The method of claim 11, further comprising the step of displaying on a screen the captured image including the calibration slate appearing in the image and a second color chart comprising a set of colors having known numeric color values, wherein each color in the set on the second color chart is substantially similar to a corresponding color associated with the batch of calibration slates.

15. The method of claim 11, wherein the step of positioning the calibration slate in a location adjacent to the wound comprises attaching the calibration slate to the patient in a location adjacent to the wound using an adhesive attached to the calibration slate.

16. The method of claim 11, further comprising the step of associating the calibration slate appearing in the image with the patient based on patient identification information included on the calibration slate.

17. The method of claim 16, wherein the patient identification information is machine-readable, wherein the method further comprises the step of reading the patient identification information.

18. The method of claim 11, wherein the calibration slate appearing in the image further includes a focus chart comprising concentrically arranged shapes, wherein the focus chart is configured such that it can be used for grading the focus of the image, wherein the method further comprises the step of focusing the image using the focus chart before capturing the image.

19. The method of claim 11, further comprising the step of adding a security mark to the captured image, wherein the security mark is configured to indicate whether the image has been altered.

20. The method of claim 11, further comprising the steps of: adding a machine-readable unique number to the captured image for indicating that the image is certified, and certifying the image by reading the unique number.

* * * * *